United States Patent

Bajgrowicz et al.

Patent Number: 5,101,048
Date of Patent: Mar. 31, 1992

[54] β-D-PHENYLTHIOXYLOSIDES, THEIR METHOD OF PREPARATION AND THEIR USE AS THERAPEUTIC AGENTS

[75] Inventors: Jerzy Bajgrowicz, Dijon; Patrice Renaut, Fontaine les Dijon; Véronique Barberousse, Dijon; Soth Samreth, Longvic; Jean Millet, Saulon la Rue; François Bellamy, Saulon la Chapelle, all of France

[73] Assignee: Fournier Industrie Et Sante, Paris, France

[21] Appl. No.: 423,958

[22] Filed: Oct. 18, 1989

[30] Foreign Application Priority Data

Oct. 18, 1988 [FR] France .................. 88 13688
Jun. 21, 1989 [FR] France .................. 89 08253

[51] Int. Cl.$^5$ .................................. C07D 335/02
[52] U.S. Cl. .................................. 549/28
[58] Field of Search ............ 549/28; 514/459, 460

[56] References Cited

U.S. PATENT DOCUMENTS

| | | | |
|---|---|---|---|
| 3,243,425 | 3/1966 | Whistler | 536/4.1 |
| 4,584,012 | 4/1986 | Singh | 71/93 |
| 4,877,808 | 10/1989 | Samreth et al. | 549/28 X |

FOREIGN PATENT DOCUMENTS

| | | |
|---|---|---|
| 0008881 | 3/1980 | European Pat. Off. |
| 0118676 | 9/1984 | European Pat. Off. |
| 0133103 | 2/1985 | European Pat. Off. |
| 0224849 | 6/1987 | European Pat. Off. |

*Primary Examiner*—C. Warren Ivy
*Assistant Examiner*—Catherine S. Kilby Scalzo
*Attorney, Agent, or Firm*—Fleit, Jacobson, Cohn, Price, Holman & Stern

[57] ABSTRACT

The present invention relates, by way of novel industrial products, to the β-D-phenylthioxyloside compounds of the formula

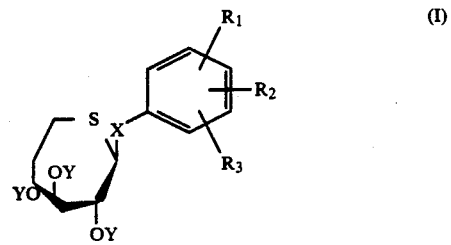

in which:

X represents a sulfur atom or an oxygen atom;

$R_1$, $R_2$ and $R_3$, which are identical or different, each represent a hydrogen atom, a nitro group, a cyano group, a group —CO—R (in which R represents a $C_1$-$C_4$ alkyl group or a trifluoromethyl group), an amino group, an acetamido group ($NHCOCH_3$), a $C_1$-$C_4$ alkoxy group, a trifluoromethyl group or a phenyl group substituted by one or more cyano, nitro or trifluoromethyl groups, it being possible for $R_1$ and $R_2$, taken together, to form, with the phenyl group to which they are bonded, a β-naphthalenyl group which is unsubstituted or substituted by one or more cyano, nitro or trifluoromethyl groups; and Y represents the hydrogen atom or an aliphatic acyl group.

These compounds are useful as therapeutic agents, especially as venous antithrombotics.

6 Claims, No Drawings

β-D-PHENYLTHIOXYLOSIDES, THEIR METHOD OF PREPARATION AND THEIR USE AS THERAPEUTIC AGENTS

The present invention relates, by way of novel industrial products, to the β-D-phenylthioxyloside compounds of formula I below. It further relates to their method of preparation and their use in therapy as antithrombotics, especially venous antithrombotics.

European patent document B-0051023 has already disclosed benzoylphenyloside and α-hydroxybenzylphenyloside derivatives as ulcer inhibitors, platelet aggregation inhibitors, antithrombotics and cerebral oxygenators.

Also, European patent document A-0133103 has disclosed benzylphenylosides which are useful as hypocholesterolemics and hypolipidemics, some of these compounds, in particular the product of Example 1, having antithrombotic effects as well.

It has now just been found that the β-D-phenylthioxyloside compounds according to the invention, which are structurally different from the known products of the prior art, are useful in the treatment and prevention of diseases associated with circulatory disorders, especially as venous antithrombotics.

The compounds according to the invention unexpectedly have antithrombotic properties which are greatly superior to those of the known products of the prior art; reference is made in this connection to the results of the comparative experiments collated in Table I below.

The novel products according to the invention are selected from the group consisting of the β-D-phenylthioxylosides of the formula

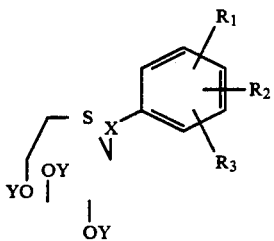

in which:

X represents a sulfur atom or an oxygen atom;

$R_1$, $R_2$ and $R_3$, which are identical or different, each represent a hydrogen atom, a nitro group, a cyano group, a group —CO—R (in which R represents a $C_1$–$C_4$ alkyl group or a trifluoromethyl group), an amino group, an acetamido group ($NHCOCH_3$), a $C_1$–$C_4$ alkoxy group, a trifluoromethyl group or a phenyl group substituted by one or more cyano, nitro or trifluoromethyl groups, it being possible for $R_1$ and $R_2$, taken together, to form, with the phenyl group to which they are bonded, a β-naphthalenyl group which is unsubstituted or substituted by one or more cyano, nitro or trifluoromethyl groups; and Y represents the hydrogen atom or an aliphatic acyl group.

The hydroxyl groups of the β-D-thioxylose residue are capable of being acylated, especially acetylated. The present invention therefore includes the derivatives of formula I in which the hydroxyl groups of the β-D-thioxylose residue are acylated, especially acetylated.

Among the aliphatic acyl groups which are suitable according to the invention, there may be mentioned those which contain a total of 2 to 5 carbon atoms, the preferred aliphatic acyl group being $CH_3CO$.

$C_1$–$C_4$ alkyl group is understood here as meaning a linear or branched hydrocarbon radical containing 1 to 4 carbon atoms, the preferred alkyl group being the methyl group.

$C_1$–$C_4$ alkoxy group is understood here as meaning an alkoxy group in which the linear or branched hydrocarbon radical contains 1 to 4 carbon atoms, the preferred alkoxy group being the methoxy group.

The preferred compounds according to the invention are the compounds of formula I in which:

X represents a sulfur atom or an oxygen atom;

$R_1$ represents the hydrogen atom;

at least one of the radicals $R_2$ and $R_3$ represents a cyano group or $R_2$ represents the hydrogen atom and $R_3$ represents a 4-acetyl group, a 4-acetamido group or a 2-nitro group; and Y represents the hydrogen atom or a $C_2$–$C_5$ aliphatic acyl group.

The compounds of formula I and the corresponding acylated compounds can be prepared by means of a glycosylation reaction which comprises:

(i) reacting a compound of the formula

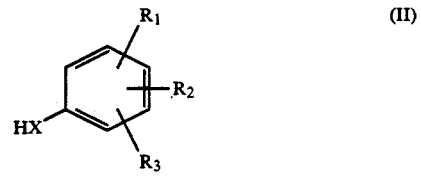

in which X, $R_1$, $R_2$ and $R_3$ are as defined above, with a thioxylose derivative selected from the group consisting of:

(i) the acylthioxylosyl halides of the formula

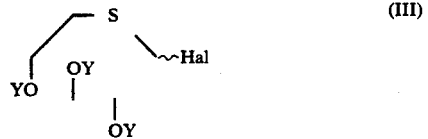

(ii) the peracylated thioxyloses of the formula

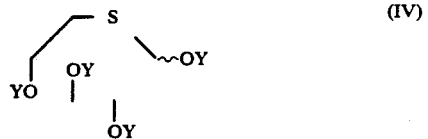

and (iii) the acylthioxylosyl trichloroacetimidates of the formula

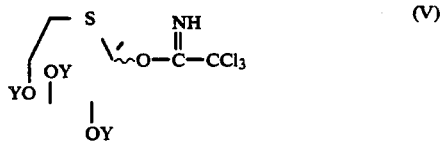

in which Hal represents a halogen atom such as Cl or Br (the bromine atom being the preferred halogen atom here) and Y represents an acyl group, especially an aliphatic acyl group containing a total of 2 to 5 carbon atoms and preferably the acetyl group, in an inert solvent, at a rate of 1 mol of II to about 0.6 to 1.2 mol of compound III, IV or V, in the presence of an acid acceptor and/or a Lewis acid; and (ii) if necessary, carrying out a deacylation reaction at a temperature in the range from 0° C. to the reflux temperature in the range from 0° C. to the reflux temperature of the reaction medium, in a $C_1$–$C_4$ lower alcohol (preferably methanol), in the presence of a metal alcoholate (preferably magnesium methylate or sodium methylate), to give a compound of formula I in which Y is H.

Compounds III, IV and V can be in the $\alpha$ or $\beta$ configuration or in the form of an anomeric mixture of both configurations.

The glycosylation reactions of phenols and thiophenols II were carried out either starting from compound III in the presence of a catalyst such as salts or oxides of silver, mercury or zinc, or starting from compound V in the presence of a Lewis acid, especially boron trifluoride etherate or zinc chloride, or starting from compound IV in the presence of a Lewis acid.

According to one preferred way of carrying out the invention, it is recommended to condense 1 mol of phenol or thiophenol II with about 1.1 to 1.2 mol of acylthioxylosyl halide III in an inert solvent selected from polar or apolar solvents (for example dimethylformamide, tetrahydrofuran, dioxane, acetonitrile, nitromethane, benzene, toluene, xylenes and mixtures thereof), in the presence of mercuric cyanide.

It will be advantageous to use 2,3,4-tri-O-acetyl-5-thio-$\alpha$-D-xylopyranosyl bromide in a benzene/nitromethane mixture (1/1 v/v), in the presence of 1.1 to 1.3 mol of mercuric cyanide, at a temperature in the range from 0° C. to the reflux temperature of the reaction medium, preferably at about 40°–50° C., for 1 to 4 hours, preferably for about 2 hours.

According to a second preferred way of carrying out the invention, it is recommended to condense 1 mol of phenol or thiophenol II with about 1.1 to 1.2 mol of acylthioxylosyl halide III in an inert solvent (for example methylene chloride or acetonitrile), in the presence of silver imidazolate and zinc chloride.

It will be advantageous to use 2,3,4-tri-O-acetyl-5-thio-D-xylopyranosyl bromide in methylene chloride or a methylene chloride/acetonitrile mixture, in the presence of 1.5 to 1.7 mol of silver imidazolate and 2 to 2.2 mol of zinc chloride, at a temperature in the range from 0° C. to the reflux temperature of the reaction medium, preferably at about 40°–60° C., for 24 to 48 hours.

According to a third preferred way of carrying out the invention, it is recommended to condense 1 mol of phenol or thiophenol II with about 0.6 to 1 mol of acylthioxylosyl halide III in an inert solvent (for example toluene and/or acetonitrile), in the presence of zinc oxide.

It will be advantageous to use 2,3,4-tri-O-acetyl-5-thio-D-xylopyranosyl bromide in a toluene/acetonitrile mixture, in the presence of 0.5 to 1.2 mol of zinc oxide, at a temperature in the range from room temperature to the reflux temperature of the reaction medium, preferably at about 40°–60° C., for 18 to 48 hours.

According to a fourth preferred way of carrying out the invention, it is recommended to condense 1 mol of phenol or thiophenol II with about 1.1 to 1.3 mol of acylthioxylosyl trichloroacetimidate in an inert solvent (for example methylene chloride), in the presence of boron trifluoride etherate.

It will be advantageous to use 2,3,4-tri-O-acetyl-5-thio-$\alpha$-D-xylopyranosyl trichloroacetimidate in methylene chloride, in the presence of 0.1 to 0.4 mol of boron trifluoride etherate dissolved in methylene chloride, or zinc chloride, at a temperature in the range from $-40°$ C. to room temperature (15°–25° C.), preferably at about $-20°$ C. to 0° C., for 1 to 5 hours.

In all cases the glycosylation reaction yields a mixture of the isomers of $\alpha$ and $\beta$ configuration in variable proportions.

The isomer of $\beta$ configuration is isolated by the methods known to those skilled in the art, for example fractional crystallization or chromatography, especially flash chromatography (i.e. chromatography on a silica column, under pressure, according to the technique described by W. C. STILL et al. in J. Org. Chem. (1978), 42 (no. 14) 2923).

If appropriate, the derivatives obtained are subjected to deacylation, more particularly to deacetylation, which is carried out at a temperature in the range from 0° C. to the reflux temperature of the reaction medium, in a $C_1$–$C_4$ lower alcohol, in the presence of the corresponding metal alcoholate. Preferably, methanol will be chosen as the lower alcohol and sodium or magnesium methanolate as the metal alcoholate.

If desired, the deacylation reaction can be carried out after glycosylation without isolation of the intermediate acylated compound formed.

It is also possible to carry out the deacylation reaction enzymatically, for example using pork liver esterase.

The acylthioxylosyl halides of formula III of $\beta$ configuration in which Y represents an aliphatic acyl group containing 2 to 5 carbon atoms are novel compounds.

The acylthioxylosyl trichloroacetimidates of formula V in which Y represents an aliphatic acyl group containing 2 to 5 carbon atoms are novel compounds.

To obtain the intermediate thiophenols of formula II in which X=S, it is recommended to:

(i) condense dimethylaminothiocarbamoyl chloride of the formula

(VI)

in a strong basic medium, with a phenol of the formula

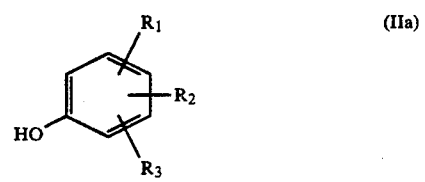
(IIa)

in which $R_1$, $R_2$ and $R_3$ are as defined above, to give a compound of the formula

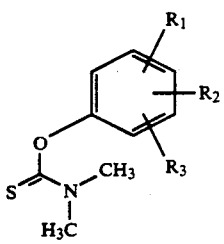

in which $R_1$, $R_2$ and $R_3$ are as defined above;

(ii) subject the resulting compound of formula VII to a Newmann rearrangement (J. Org. Chem. (1966) 31, p. 3980), by heating, to give a compound of the formula

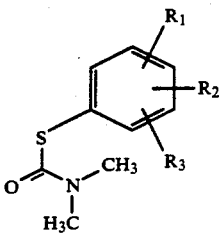

in which $R_1$, $R_2$ and $R_3$ are as defined above; and (iii) treat the resulting compound of formula VIII with a metal alcoholate, preferably sodium or magnesium methanolate, in a $C_1$–$C_4$ lower alcohol, preferably methanol, dimethylformamide or dioxane, to give a thiophenol of formula II in which X=S.

The intermediate thiophenols can also be obtained by the nucleophilic substitution of an appropriate halogenobenzene according to the method described by L. TESTAFERRI in Tetrahedron Letters, vol. 21, p. 3099-3100 (1980) or according to the method described by Paolo BATTISTONI in Gazzetta Chimica Italiana, 110, p. 301 (1980).

The following thiophenols are novel compounds: 3,5-bis(trifluoromethyl)benzenethiol, 3-cyano-4-mercaptobenzonitrile, 6-mercaptonaphthalene-2-carbonitrile and 3,5-dicyano-2-mercaptobenzonitrile.

The following dimethylthiocarbamates are novel compounds: O-4-trifluoromethylphenyl dimethylthiocarbamate, O-3-cyanophenyl dimethylthiocarbamate, O-2-cyanophenyl dimethylthiocarbamate, O-2-(6-cyanonaphthalenyl)dimethylthiocarbamate, O-3,4,5-trimethoxyphenyl dimethylthiocarbamate, O-2-trifluoromethylphenyl dimethylthiocarbamate, O-3,5-bis(-trifluoromethyl)phenyl dimethylthiocarbamate, O-2,4-dicyanophenyl dimethylthiocarbamate, O-4-(4-cyanophenyl)phenyl dimethylthiocarbamate, O-2,4,6-tricyanophenyl dimethylthiocarbamate, S-4-trifluoromethylphenyl dimethylthiocarbamate, S-3-cyanophenyl dimethylthiocarbamate, S-2-cyanophenyl dimethylthiocarbamate, S-2-(6-cyanonaphthalenyl)-dimethylthiocarbamate, S-3,4,5-trimethoxyphenyl dimethylthiocarbamate, S-2-trifluoromethylphenyl dimethylthiocarbamate, S-3,5-bis(trifluoromethyl)phenyl dimethylthiocarbamate, S-2,4-dicyanophenyl dimethylthiocarbamate, S-4-(4-cyanophenyl)phenyl dimethylthiocarbamate and S-2,4,6-tricyanophenyl dimethylthiocarbamate.

According to the invention, a therapeutic composition is proposed which contains, in association with a physiologically acceptable excipient, at least one compound selected from the group consisting of the products of formula I. Of course, in such a composition, the active ingredient is present in a therapeutically effective amount.

The compounds of formula I are useful in therapy as antithrombotics. They are particularly useful in the prevention and treatment of disorders of the venous circulation.

According to the invention, it is recommended to use a substance belonging to the group consisting of the compounds of formula I in order to obtain an antithrombotic drug for use in therapy to combat disorders of the venous circulation.

Further characteristics and advantages of the invention will be understood more clearly from the following description of Preparatory Examples, which in no way imply a limitation and are given by way of illustration, and results of pharmacological experiments.

In the following Preparatory Examples, the α or β configuration has been specified in the compound names in cases where said configuration was determined. Where the configuration is not indicated, this means that the corresponding product is an anomeric mixture of the α and β configurations in proportions which were not determined.

PREPARATION I

Preparation of 4-cyanophenyl 2,3,4-tri-O-acetyl-1,5-dithio-β-D-xylopyranoside (Example 1a)

Under an inert atmosphere, a mixture of 70 ml of anhydrous benzene, 70 ml of nitromethane and 15 g of a 0.4 nm molecular sieve (marketed by E. MERCK) is stirred at room temperature (15°–25° C.) for 0.25 h and 12 g ($47.10^{-3}$ mol) of $Hg(CN)_2$ are then added. After the resulting mixture has been stirred for 10 minutes at room temperature, 16.9 g ($47.10^{-3}$ mol) of 2,3,4-tri-O-acetyl-5-thio-α-D-xylopyranosyl bromide and then 6 g ($43.10^{-3}$ mol) of 4-mercaptobenzonitrile are added in small portions. When the addition is complete, the reaction mixture is heated at 40°–50° C. for 8 hours and then filtered on Célite ® (i.e. diatomaceous silica for filtration). The residue is washed several times with ethyl acetate. The organic phase is collected and washed successively with a 1N aqueous solution of hydrochloric acid, a 1N aqueous solution of sodium hydroxide and a saturated solution of sodium chloride and then with water until the pH of the washings is neutral; it is dried over magnesium sulfate and filtered and the solvent is evaporated off. The crude product obtained is recrystallized from an ethyl acetate/petroleum ether mixture to give 8.65 g (yield: 49%) of the product of β configuration.

M.p.=155° C.

$[\alpha]_D^{20\ C.}=+37°$ (c=0.5; $CHCl_3$)

PREPARATION II

Preparation of 4-cyanophenyl 2,3,4-tri-O-acetyl-1,5-dithio-β-D-xylopyranoside (Example 1a)

A suspension of 625 mg ($1.76.10^{-3}$ mol) of 2,3,4-tri-O-acetyl-5-thio-D-xylopyranosyl bromide, 200 mg ($1.48.10^{-3}$ mol) of 4-mercaptobenzonitrile and a 400 pm molecular sieve in 10 ml of acetonitrile is stirred in the presence of 605 mg ($4.4.10^{-3}$ mol) of zinc chloride and 310 mg ($1.8.10^{-3}$ mol) of silver imidazolate, in the absence of light, under an inert atmosphere. After heating at 50° C. for 3 h, the reaction mixture is filtered on Célite® in ethyl acetate. The filtrate is washed with a 1N solution of hydrochloric acid, water, a 1N solution of sodium hydroxide, water and finally a saturated solution of sodium chloride, dried over magnesium sulfate and evaporated under reduced pressure. After purification by chromatography on silica gel using a hexane/ethyl acetate mixture (3/1 v/v) as the eluent, and precipitation in ether, 100 mg (yield: 17%) of the expected product are obtained.

M.p.=155° C.

PREPARATION III

Preparation of 4-cyanophenyl 2,3,4-tri-O-acetyl-1,5-dithio-β-D-xylopyranoside (Example 1a)

A suspension of 192 mg ($0.44.10^{-3}$ mol) of 2,3,4-tri-O-acetyl-5-thio-α-D-xylopyranosyl trichloroacetimidate, 71 mg ($0.52.10^{-3}$ mol) of 4-mercaptobenzonitrile, 20 mg ($0.15.10^{-3}$ mol) of zinc chloride and a 400 pm sieve in 2 ml of acetonitrile is stirred for 4 h under an inert atmosphere. The reaction mixture is then filtered on Célite® in ethyl acetate and subsequently washed with a 1N solution of sodium hydroxide, water and finally a saturated solution of sodium chloride, dried over magnesium sulfate and evaporated under reduced pressure. After precipitation in ether, 42 mg (yield: 23%) of the expected product are obtained.

M.p.=155° C.

PREPARATION IV

Preparation of 4-cyanophenyl 2,3,4-tri-O-acetyl-1,5-dithio-β-D-xylopyranoside (Example 1a)

A suspension of 16.9 g ($47.10^{-3}$ mol) of 2,3,4-tri-O-acetyl-5-thio-α-D-xylopyranosyl bromide, 6 g ($43.10^{-3}$ mol) of 4-mercaptobenzonitrile and 3.5 g ($43.10^{-3}$ mol) of zinc oxide (ZnO) in 120 ml of anhydrous toluene and 120 ml of acetonitrile is stirred under an inert atmosphere, in the presence of a molecular sieve (1 mm), for 18 hours, at 50° C. After the reaction medium has been filtered on Célite® in ethyl acetate, the organic phase obtained is washed with a 1N solution of HCl twice, a 1N solution of sodium hydroxide and finally water, dried over magnesium sulfate and evaporated under reduced pressure. After precipitation in ether, 11.30 g (yield: 64%) of the expected product are obtained.

M.p.=155° C.

PREPARATION V

Preparation of 4-cyanophenyl 1,5-dithio-β-D-xylopyranoside (Example 1)

Under a nitrogen atmosphere, 8.5 g ($21.10^{-3}$ mol) of 4-cyanophenyl 2,3,4-tri-O-acetyl-1,5-dithio-β-D-xylopyranoside (Example 1a) are suspended in 100 ml of methanol, and 2 ml of sodium methylate (8% w/v of Na in methanol) are then added. The reaction medium is stirred at room temperature until the starting material has completely dissolved (2 hours) and is then neutralized by the addition of Amberlite® IR 120 H+ resin. The methanol is evaporated off under reduced pressure; the crude product obtained is recrystallized from an ethanol/water mixture (65/25 v/v) to give 5.3 g (yield: 89.7%) of the expected product.

M.p.=175° C.

$[\alpha]_D^{20° C.} = +35.8°$ (c=0.5; CH$_3$OH)

PREPARATION VI

Preparation of 4-nitrophenyl 2,3,4-tri-O-acetyl-1,5-dithio-β-D-xylopyranoside (Example 2a)

If the procedure described in Preparation I is followed starting from 6 g ($38.10^{-3}$ mol) of 4-nitrobenzenethiol, 10.7 g ($42.10^{-3}$ mol) of mercuric cyanide, Hg(CN)$_2$, and 15.1 g ($42.10^{-3}$ mol) of 2,3,4-tri-O-acetyl-5-thio-α-D-xylopyranosyl bromide, 10.8 g (yield: 66%) of the expected product are obtained.

M.p.=182° C.

$[\alpha]_D^{20° C.} = +50.8°$ (c=0.64; CHCl$_3$)

PREPARATION VII

Preparation of 4-nitrophenyl 2,3,4-tri-O-acetyl-1,5-dithio-β-D-xylopyranoside (Example 2a)

If the procedure described in Preparation IV is followed starting from 6 g ($38.10^{-3}$ mol) of 4-nitrobenzenethiol, 15.1 g ($42.10^{-3}$ mol) of 2,3,4-tri-O-acetyl-5-thio-α-D-xylopyranosyl bromide and 3.2 g ($39.10^{-3}$ mol) of zinc oxide (ZnO), 13 g (yield: 79%) of the expected product are obtained after precipitation in ether.

M.p.=182° C.

PREPARATION VIII

Preparation of 4-nitrophenyl 1,5-dithio-β-D-xylopyranoside (Example 2)

If the procedure described in Preparation V is followed starting from 10.3 g ($24.10^{-3}$ mol) of 4-nitrophenyl 2,3,4-tri-O-acetyl-1,5-dithio-β-D-xylopyranoside (Example 2a), 5.4 g (yield: 74%) of the expected product are obtained after recrystallization from an ethanol/water mixture (1/1 v/v).

M.p.=168° C.

$[\alpha]_D^{20° C.} = +54°$ (c=0.64; CH$_3$OH)

PREPARATION IX

Preparation of 2-naphthalenyl 2,3,4-tri-O-acetyl-1,5-dithio-β-D-xylopyranoside (Example 3a)

If the procedure described in Preparation I is followed starting from 6.8 g ($42.4.10^{-3}$ mol) of naphthalene-2-thiol, 10.8 g ($42.4.10^{-3}$ mol) of mercuric cyanide, Hg(CN)$_2$, and 12 g ($33.2.10^{-3}$ mol) of 2,3,4-tri-O-acetyl-5-thio-α-D-xylopyranosyl bromide, 5.84 g (yield: 40%) of the expected product are obtained.

M.p.=151° C.

$[\alpha]_D^{20° C.} = -41.5°$ (c=1.6; CHCl$_3$)

PREPARATION X

Preparation of 2-naphthalenyl 1,5-dithio-β-D-xylopyranoside (Example 3)

If the procedure described in Preparation V is followed starting from 5.8 g ($13.10^{-3}$ mol) of 2-naphthalenyl 2,3,4-tri-O-acetyl-1,5-dithio-α-D-xylopyranoside (Example 3a), 3.45 g (yield: 86%) of the expected product are obtained after recrystallization from an ethanol/water mixture (4/1 v/v).

M.p.=163°-164° C.

$[\alpha]_D^{20° C.} = +31.1°$ (c=0.9; CH$_3$OH)

PREPARATION XI

Preparation of O-4-trifluoromethylphenyl dimethylthiocarbamate 10 g ($62.10^{-3}$ mol) of 4-trifluoromethylphenol are added to a solution of 3.63 g ($65.10^{-3}$ mol) of potassium hydroxide in 100 ml of water and 100 ml of acetone. The mixture obtained is stirred for 45 minutes at room temperature and then cooled to 0° C. before the addition of 8.77 g ($71.10^{-3}$ mol) of dimethylthiocarbamoyl chloride. The resulting reaction medium is subsequently stirred for 4 hours at room temperature and then hydrolyzed. The expected product is extracted with ethyl acetate. The resulting organic phase is washed with a 1N aqueous solution of sodium hydroxide, then a 1N aqueous solution of hydrochloric acid and finally water, after which it is dried and evaporated under reduced pressure to give 17 g (quantitative yield) of the expected product.

PREPARATION XII

Preparation of S-4-trifluoromethylphenyl dimethylthiocarbamate

Under a nitrogen atmosphere, 17 g ($68.10^{-3}$ mol) of O-4-trifluoromethylphenyl dimethylthiocarbamate are heated at 220° C. for 5 hours. After purification by flash chromatography using a toluene/ethyl acetate mixture (8/1 v/v) as the eluent, 13 g (yield: 80%) of the expected product are obtained.

PREPARATION XIII

Preparation of 4-trifluoromethylbenzenethiol

Under a nitrogen atmosphere, 12 g ($48.10^{-3}$ mol) of S-4-trifluoromethylphenyl dimethylthiocarbamate are dissolved in 125 ml of dimethylformamide. The solution obtained is cooled to 0° C. and 25 ml of an 18% solution of sodium methylate in methanol are then added. After stirring for 1.5 hours, the reaction medium is hydrolyzed in a 1N hydrochloric acid/ice mixture and then extracted with ethyl acetate. The organic phase obtained is washed with water, dried over magnesium sulfate and then evaporated under reduced pressure. 6.2 g (yield: 67%) of the expected product are obtained after purification by flash chromatography using a hexane/ethyl acetate mixture (8/1 v/v) as the eluent.

PREPARATION XIV

Preparation of 4-trifluoromethylphenyl 2,3,4-tri-O-acetyl-1,5-dithio-β-D-xylopyranoside (Example 4a)

If the procedure described in Preparation I is followed starting from 5.58 g ($32.10^{-3}$ mol) of 4-trifluoromethylbenzenethiol, 8.87 g ($35.10^{-3}$ mol) of mercuric cyanide, $Hg(CN)_2$, and 12.3 g ($35.10^{-3}$ mol) of 2,3,4-tri-O-acetyl-5-thio-α-D-xylopyranosyl bromide, 6.2 g (yield: 40%) of the expected product are obtained.

M.p.=160° C.

$[\alpha]_D^{20°\,C.} = +16°$ (c=0.5; $CHCl_3$)

PREPARATION XV

Preparation of 4-trifluoromethylphenyl 2,3,4-tri-O-acetyl-1,5-dithio-β-D-xylopyranoside (Example 4a)

If the procedure described in Preparation IV is followed starting from 5.6 g ($32.10^{-3}$ mol) of 4-trifluoromethylbenzenethiol, 12.3 g ($35.10^{-3}$ mol) of 2,3,4-tri-O-acetyl-5-thio-α-D-xylopyranosyl bromide and 2.55 g ($32.10^{-3}$ mol) of zinc oxide (ZnO), 7.4 g (yield: 48%) of the expected product are obtained after precipitation in ether.

M.p.=160° C.

PREPARATION XVI

Preparation of 4-trifluoromethylphenyl 1,5-dithio-β-D-xylopyranoside (Example 4)

If the procedure described in Preparation V is followed starting from 6.2 g ($14.10^{-3}$ mol) of 4-trifluoromethylphenyl 2,3,4-tri-O-acetyl-1,5-dithio-β-D-xylopyranoside (Example 4a), 2.05 g (yield: 45%) of the expected product are obtained after purification by flash chromatography using a $CHCl_3/CH_3OH$ mixture (4/1 v/v) as the eluent.

M.p.=128°-130° C.

$[\alpha]_D^{23°\,C.} = +10°$ (c=0.5; $CH_3OH$)

PREPARATION XVII

Preparation of O-3-cyanophenyl dimethylthiocarbamate

If the procedure described in Preparation XI is followed starting from 15 g ($126.10^{-3}$ mol) of 3-hydroxybenzonitrile, 17.9 g ($145.10^{-3}$ mol) of dimethylthiocarbamoyl chloride and 7.4 g ($132.10^{-3}$ mol) of potassium hydroxide, 29 g (quantitative yield) of the expected product are obtained.

M.p.=108° C.

PREPARATION XVIII

Preparation of S-3-cyanophenyl dimethylthiocarbamate

If the procedure described in Preparation XII is followed starting from 29 g ($141.10^{-3}$ mol) of O-3-cyanophenyl dimethylthiocarbamate, 19 g (yield: 65.5%) of the expected product are obtained.

M.p.=104° C.

PREPARATION XIX

Preparation of 3-mercaptobenzonitrile

If the procedure described in Preparation XIII is followed starting from 19 g ($92.10^{-3}$ mol) of O-3-cyanophenyl dimethylthiocarbamate, 10.3 g (yield: 83.1%) of the expected product, melting at 91°-95° C., are obtained.

PREPARATION XX

Preparation of 3-cyanophenyl 2,3,4-tri-O-acetyl-1,5-dithio-β-D-xylopyranoside (Example 5a)

If the procedure described in Preparation I is followed starting from 9.3 g ($67.10^{-3}$ mol) of 3-mercaptobenzonitrile, 18 g ($73.10^{-3}$ mol) of mercuric cyanide, $Hg(CN)_2$, and 26.14 g ($73.10^{-3}$ mol) of 2,3,4-tri-O-acetyl-5-thio-α-D-xylopyranosyl bromide, 8.55 g of the expected product are obtained.

M.p.=133° C.

$[\alpha]_D^{20°\,C.} = +0.9°$ (c=0.44; $CHCl_3$)

PREPARATION XXI

Preparation of 3-cyanophenyl 2,3,4-tri-O-acetyl-1,5-dithio-β-D-xylopyranoside (Example 5a)

If the procedure described in Preparation IV is followed starting from 10.3 g ($74.1.10^{-3}$ mol) of 3-mercaptobenzonitrile, 28.94 g (81.5.10$^{-3}$ mol) of 2,3,4-tri-O-acetyl-5-thio-α-D-xylopyranosyl bromide and 6.05 g (74.3.10$^{-3}$ mol) of zinc oxide (ZnO), 9.6 g (yield: 31%) of the expected product are obtained.

M.p.=133° C.

PREPARATION XXII

Preparation of 3-cyanophenyl 1,5-dithio-β-D-xylopyranoside (Example 5)

If the procedure described in Preparation V is followed starting from 8.50 g (20.10$^{-3}$ mol) of 3-cyanophenyl 2,3,4-tri-O-acetyl-1,5-dithio-β-D-xylopyranoside, 3.10 g (yield: 54.3%) of the expected product are obtained after recrystallization from methanol.

M.p.=194°-195° C.
$[\alpha]_D^{20°\ C.} = -5.4°$ (c=0.48; CH$_3$OH)

PREPARATION XXIII

Preparation of O-2-cyanophenyl dimethylthiocarbamate

If the procedure described in Preparation XVI is followed starting from 15 g (126.10$^{-3}$ mol) of 2-hydroxybenzonitrile, 17.9 g (145.10$^{-3}$ mol) of dimethylthiocarbamoyl chloride and 7.4 g (126.10$^{-3}$ mol) of potassium hydroxide, 24.1 g (yield: 94%) of the expected product are obtained.

M.p.=112° C.

PREPARATION XXIV

Preparation of S-2-cyanophenyl dimethylthiocarbamate

If the procedure described in Preparation XII is followed starting from 28 g (136.10$^{-3}$ mol) of O-2-cyanophenyl dimethylthiocarbamate, 20 g (yield: 71.4%) of the expected product are obtained.

M.p.=70° C.

PREPARATION XXV

Preparation of 2-mercaptobenzonitrile

If the procedure described in Preparation XIII is followed starting from 20 g (97.10$^{-3}$ mol) of S-2-cyanophenyl dimethylthiocarbamate, 10.9 g (yield: 83.2%) of the expected product are obtained in the form of an oil.

$n_D$=1.496

PREPARATION XXVI

Preparation of 2-cyanophenyl 2,3,4-tri-O-acetyl-1,5-dithio-β-D-xylopyranoside (Example 6a)

If the procedure described in Preparation I is followed starting from 9.70 g (72.10$^{-3}$ mol) of 2-mercaptobenzonitrile, 19.45 g (77.10$^{-3}$ mol) of mercuric cyanide, Hg(CN)$_2$, and 27.4 g (77.10$^{-3}$ mol) of 2,3,4-tri-O-acetyl-5-thio-α-D-xylopyranosyl bromide, 14.7 g (yield: 50%) of the expected product are obtained.

M.p.=160° C.
$[\alpha]_D^{20°\ C.} = -45.5°$ (c=0.4; CHCl$_3$)

PREPARATION XXVII

Preparation of 2-cyanophenyl 2,3,4-tri-O-acetyl-1,5-dithio-β-D-xylopyranoside (Example 6a)

If the procedure described in Preparation IV is followed starting from 10.7 g (79.2.10$^{-3}$ mol) of 2-mercaptobenzonitrile, 30.2 g (85.10$^{-3}$ mol) of 2,3,4-tri-O-acetyl-5-thio-α-D-xylopyranosyl bromide and 6.3 g (77.4.10$^{-3}$ mol) of zinc oxide (ZnO), 19.3 g (yield: 60%) of the expected product are obtained after crystallization from ether.

M.p.=160° C.

PREPARATION XXVIII

Preparation of 2-cyanophenyl 1,5-dithio-β-D-xylopyranoside (Example 6)

If the procedure described in Preparation V is followed starting from 14.5 g (35.10$^{-3}$ mol) of 2-cyanophenyl 2,3,4-tri-O-acetyl-1,5-dithio-β-D-xylopyranoside (Example 6a), 8.39 g (yield: 84.6%) of the expected product are obtained after recrystallization from methanol.

M.p.=118°-119° C.
$[\alpha]_D^{20°\ C.} = +12.5°$ (c=0.52; CH$_3$OH)

PREPARATION XXIX

Preparation of 2-nitrobenzenethiol 15.24 g (63.4.10$^{-3}$ mol) of sodium sulfide (Na$_2$S.9-H$_2$O) are added to a solution of 10 g (63.4.10$^{-3}$ mol) of 2-chloronitrobenzene. The solution obtained is stirred at room temperature for 12 hours. The reaction medium is hydrolyzed in an ice/1N hydrochloric acid mixture. The yellow precipitate formed is filtered off and the mother liquors are extracted with ethyl acetate. The resulting organic phase is washed with water until the pH of the washings is neutral, dried over magnesium sulfate and evaporated under reduced pressure to give 5.2 g of an oil, which are added to the 3.8 g of precipitate. These 9 g of resulting product are purified by chromatography on silica using a hexane/acetone mixture (95/5 v/v) as the eluent to give 6.02 g (yield: 61%) of the expected product.

PREPARATION XXX

Preparation of 2-nitrophenyl 2,3,4-tri-O-acetyl-1,5-dithio-β-D-xylopyranoside (Example 7a)

If the procedure described in Preparation I is followed starting from 6 g (38.7.10$^{-3}$ mol) of 2-nitrobenzenethiol, 10.75 g (42.5.10$^{-3}$ mol) of mercuric cyanide, Hg(CN)$_2$, and 15.12 g (42.10$^{-3}$ mol) of 2,3,4-tri-O-acetyl-5-thio-α-D-xylopyranosyl bromide, 8 g (yield: 48%) of the expected product are obtained.

M.p.=176° C.
$[\alpha]_D^{20°\ C.} = +15°$ (c=0.5; CH$_2$Cl$_2$/CH$_3$OH (1/1 v/v))

PREPARATION XXXI

Preparation of 2-nitrophenyl 2,3,4-tri-O-acetyl-1,5-dithio-β-D-xylopyranoside (Example 7a)

If the procedure described in Preparation IV is followed starting from 6.1 g (39.3.10$^{-3}$ mol) of 2-nitrobenzenethiol, 15.40 g (43.3.10$^{-3}$ mol) of 2,3,4-tri-O-acetyl-5-thio-α-D-xylopyranosyl bromide and 3.68 g (45.2.10$^{-3}$ mol) of zinc oxide (ZnO), 9.87 g (yield: 58%) of the expected product are obtained.

PREPARATION XXXII

Preparation of 2-nitrophenyl 1,5-dithio-β-D-xylopyranoside (Example 7)

If the procedure described in Preparation V is followed starting from 8 g (18.6.10$^{-3}$ mol) of 2-nitrophenyl 2,3,4-tri-O-acetyl-1,5-dithio-β-D-xylopyranoside (Example 7a), 4.68 g (yield: 83.2%) of the expected product are obtained after recrystallization from methanol.

M.p. = 185° C.
$[\alpha]_D^{20°~C.} = +12.4°$ (c=0.5; CH$_2$Cl$_2$/CH$_3$OH (1/1 v/v))

PREPARATION XXXIII

Preparation of O-2-(6-cyanonaphthalenyl)dimethylthiocarbamate 2.85 g (51.10$^{-3}$ mol) of potassium hydroxide pellets are added to a suspension of 8.05 g (47.10$^{-3}$ mol) of 2-hydroxynaphthalene-6-carbonitrile in 50 ml of acetone and 90 ml of water. The reaction mixture is heated at 50° C. for thirty minutes, with vigorous stirring. The mixture is then cooled to 0° C. and 6.46 g (52.10$^{-3}$ mol) of dimethylthiocarbamoyl chloride in 80 ml of acetone are added dropwise. When the addition is complete, the reaction medium is stirred for three hours at room temperature. It is concentrated by evaporation under reduced pressure and then hydrolyzed. 11.3 g (yield: 94%) of the expected product are obtained after filtration of the precipitate.

M.p. = 153°-154° C.

PREPARATION XXXIV

Preparation of S-2-(6-cyanonaphthalenyl)dimethylthiocarbamate

Under a nitrogen atmosphere, 10 g (39.10$^{-3}$ mol) of O-2-(6-cyanonaphthalenyl)dimethylthiocarbamate are heated at 250° C. for six hours, with stirring. The disappearance of the starting material is monitored by thin layer chromatography using an ethyl acetate/toluene mixture (1/4 v/v) as the eluent. 7.6 g (yield: 76%) of the expected product are obtained.

M.p. = 166°-168° C.

PREPARATION XXXV

Preparation of 6-mercaptonaphthalene-2-carbonitrile

Under a nitrogen atmosphere, 7.15 g (27.9.10$^{-3}$ mol) of O-2-(6-cyanonaphthalenyl)dimethylthiocarbamate are suspended in 50 ml of dioxane, with stirring, and 16 ml (55.8.10$^{-3}$ mol) of sodium methylate (8% w/v solution of Na in methanol) are then added to the mixture. The reaction medium is stirred at 21° C. for two hours and monitored by thin layer chromatography using an ethyl acetate/toluene mixture (1/3 v/v) as the eluent. The reaction medium is hydrolyzed in an ice/concentrated HCl mixture and the precipitate formed is filtered off to give 5.4 g (yield: 100%) of the expected product.

M.p. = 113°-115° C.

PREPARATION XXXVI

Preparation of 2-(6-cyanonaphthalenyl) 2,3,4-tri-O-acetyl-1,5-dithio-β-D-xylopyranoside (Example 8a)

If the procedure described in Preparation I is followed starting from 5 g (27.10$^{-3}$ mol) of 6-mercaptonaphthalene-2-carbonitrile, 7.5 g (29.10$^{-3}$ mol) of mercuric cyanide, Hg(CN)$_2$, and 12 g (32.10$^{-3}$ mol) of 2,3,4-tri-O-acetyl-5-thio-α-D-xylopyranosyl bromide, 1.6 g (yield: 12.9%) of the expected product are obtained.

M.p. = 228°-230° C.
$[\alpha]_D^{23°~C.} = +73.4°$ (c=0.5; CHCl$_3$)

PREPARATION XXXVII

Preparation of 2-(6-cyanonaphthalenyl) 2,3,4-tri-O-acetyl-1,5-dithio-β-D-xylopyranoside (Example 8a)

If the procedure described in Preparation IV is followed starting from 5 g (27.10$^{-3}$ mol) of 6-mercaptonaphthalene-2-carbonitrile, 12 g (32.4.10$^{-3}$ mol) of 2,3,4-tri-O-acetyl-5-thio-α-D-xylopyranosyl bromide and 2.2 g (27.10$^{-3}$ mol) of zinc oxide (ZnO), 1.5 g of the expected product are obtained after precipitation in ether.

M.p. = 228°-230° C.

PREPARATION XXXVIII

Preparation of 2-(6-cyanonaphthalenyl) 1,5-dithio-β-D-xylopyranoside (Example 8)

If the procedure described in Preparation V is followed starting from 1.27 g (2.76.10$^{-3}$ mol) of 2-(6-cyanonaphthalenyl) 2,3,4-tri-O-acetyl-1,5-dithio-β-D-xylopyranoside (Example 8a), 0.340 g (yield: 37%) of the expected product is obtained after recrystallization from a methanol/chloroform mixture (1/1 v/v).

M.p. = 226°-228° C.
$[\alpha]_D^{24°~C.} = +45.9°$ (c=0.3; DMSO)

PREPARATION XXXIX

Preparation of phenyl 2,3,4-tri-O-acetyl-1,5-dithio-β-D-xylopyranoside (Example 9a)

If the procedure described in Preparation I is followed starting from 4 g (36.3.10$^{-3}$ mol) of benzenethiol, 14 g (39.4.10$^{-3}$ mol) of 2,3,4-tri-O-acetyl-5-thio-α-xylopyranosyl bromide and 10 g (39.10$^{-3}$ mol) of mercuric cyanide (Hg(CN)$_2$), 7.3 g of the expected product are obtained after crystallization from ether.

M.p. = 130° C.
$[\alpha]_D^{20°~C.} = +14.6°$ (c=0.5; CHCl$_3$)

PREPARATION XL

Preparation of phenyl 2,3,4-tri-O-acetyl-1,5-dithio-β-D-xylopyranoside (Example 9a)

If the procedure described in Preparation IV is followed starting from 4 g (36.3.10$^{-3}$ mol) of benzenethiol, 15 g (42.3.10$^{-3}$ mol) of 2,3,4-tri-O-acetyl-5-thio-α-D-xylopyranosyl bromide and 3 g (36.8.10$^{-3}$ mol) of zinc oxide (ZnO), 4.5 g (yield: 32.29%) of the expected product are obtained after crystallization from ether.

M.p. = 130° C.

PREPARATION XLI

Preparation of phenyl 1,5-dithio-β-D-xylopyranoside (Example 9)

If the procedure described in Preparation V is followed starting from 6.9 g (18.10$^{-3}$ mol) of phenyl 2,3,4-tri-O-acetyl-1,5-dithio-β-D-xylopyranoside (Example 9a), 3.7 g (yield: 80%) of the expected product are obtained after recrystallization from an ethanol/water mixture (50/10 v/v).

M.p. = 150°-151° C.
$[\alpha]_D^{20°~C.} = -6°$ (c=0.5; CH$_3$OH)

PREPARATION XLII

Preparation of 3,4,5-trimethoxyphenyl 2,3,4-tri-O-acetyl-1,5-dithio-β-D-xylopyranoside (Example 10a)

If the procedure described in Preparation I is followed starting from 11.35 g ($57.10^{-3}$ mol) of 3,4,5-trimethoxybenzenethiol, 14.32 g ($57.10^{-3}$ mol) of mercuric cyanide, $Hg(CN)_2$, and 22.15 g ($62.10^{-3}$ mol) of 2,3,4-tri-O-acetyl-5-thio-α-D-xylopyranosyl bromide, 7.52 g (yield: 28%) of the expected product are obtained.

M.p. = 101° C.
$[\alpha]_D^{25°\ C.} = -43°$ (c=0.2; $CH_3OH$)

PREPARATION XLIII

Preparation of 3,4,5-trimethoxyphenyl 1,5-dithio-β-D-xylopyranoside (Example 10)

If the procedure described in Preparation V is followed starting from 4.65 g ($9.8.10^{-3}$ mol) of 3,4,5-trimethoxyphenyl 2,3,4-tri-O-acetyl-1,5-dithio-β-D-xylopyranoside (Example 10a), 2.4 g (yield: 70%) of the expected product are obtained after recrystallization from a methanol/water mixture (1/1 v/v).

M.p. = 166° C.
$[\alpha]_D^{20°\ C.} = -12°$ (c=0.2; $CH_3OH$)

PREPARATION XLIV

Preparation of 4-acetylphenyl 2,3,4-tri-O-acetyl-1,5-dithio-β-D-xylopyranoside (Example 11a)

If the procedure described in Preparation I is followed starting from 1.03 g ($6.7.10^{-3}$ mol) of 4-mercaptoacetophenone, 1.72 g ($6.8.10^{-3}$ mol) of mercuric cyanide, $Hg(CN)_2$, and 2.65 g ($7.5.10^{-3}$ mol) of 2,3,4-tri-O-acetyl-5-thio-α-D-xylopyranosyl bromide, 0.36 g (yield: 12.5%) of the expected product is obtained.

M.p. = 122° C.
$[\alpha]_D^{22°\ C.} = +46.5°$ (c=0.29; $CHCl_3$)

PREPARATION XLV

Preparation of 4-acetylphenyl 2,3,4-tri-O-acetyl-1,5-dithio-β-D-xylopyranoside (Example 11a)

If the procedure described in Preparation IV is followed starting from 1.27 g ($8.43.10^{-3}$ mol) of 4-mercaptoacetophenone, 3.27 g ($9.2.10^{-3}$ mol) of 2,3,4-tri-O-acetyl-5-thio-α-D-xylopyranosyl bromide and 0.68 g ($8.35.10^{-3}$ mol) of zinc oxide (ZnO), 0.42 g (yield: 11%) of the expected product is obtained.

M.p. = 122° C.

PREPARATION XLVI

Preparation of 4-acetylphenyl 1,5-dithio-β-D-xylopyranoside (Example 11)

If the procedure described in Preparation V is followed starting from 0.34 g ($0.8.10^{-3}$ mol) of 4-acetylphenyl 2,3,4-tri-O-acetyl-1,5-dithio-β-D-xylopyranoside (Example 11a), 0.12 g (yield: 50%) of the expected product is obtained after recrystallization from a methanol/water mixture (1/1 v/v).

M.p. = 175° C.
$[\alpha]_D^{25°\ C.} = +34°$ (c=0.2; $CH_3OH$)

PREPARATION XLVII

Preparation of 3-nitrophenyl 2,3,4-tri-O-acetyl-1,5-dithio-β-D-xylopyranoside (Example 12a)

If the procedure described in Preparation I is followed starting from 10 g ($64.5.10^{-3}$ mol) of 3-nitrobenzenethiol, 16.29 g ($64.5.10^{-3}$ mol) of mercuric cyanide ($Hg(CN)_2$) and 25.2 g ($70.9.10^{-3}$ mol) of 2,3,4-tri-O-acetyl-5-thio-α-D-xylopyranosyl bromide, 7.44 g (yield: 27%) of the expected product are obtained after purification by flash chromatography using a toluene/ethyl acetate mixture (9/1 v/v) as the eluent, followed by crystallization from ether.

M.p. = 121° C.
$[\alpha]_D^{20°\ C.} = +1.8°$ (c=0.5; $CH_3OH$)

PREPARATION XLVIII

Preparation of 3-nitrophenyl 1,5-dithio-β-D-xylopyranoside (Example 12)

If the procedure described in Preparation V is followed starting from 7.18 g ($16.7.10^{-3}$ mol) of 3-nitrophenyl 2,3,4-tri-O-acetyl-1,5-dithio-β-D-xylopyranoside (Example 12a), 3.9 g (yield: 77%) of the expected product are obtained.

M.p. = 152°–154° C.
$[\alpha]_D^{20°\ C.} = -3.6°$ (c=0.5; $CH_3OH$)

PREPARATION IL

Preparation of O-2-trifluoromethylphenyl dimethylthiocarbamate

If the procedure described in Preparation XI is followed starting from 3.95 g ($24.3.10^{-3}$ mol) of 2-trifluoromethylphenol, 1.43 g ($25.6.10^{-3}$ mol) of potassium hydroxide and 3.46 g ($28.10^{-3}$ mol) of dimethylthiocarbamoyl chloride, 5.37 g (yield: 89%) of a yellow oil are obtained.

$n_D^{24.5°\ C.} = 1.528$

PREPARATION L

Preparation of S-2-trifluoromethylphenyl dimethylthiocarbamate

If the procedure described in Preparation XII is followed starting from 5.37 g ($21.5.10^{-3}$ mol) of O-2-trifluoromethylphenyl dimethylthiocarbamate, 3.2 g (yield: 60%) of the expected product are obtained after purification by flash chromatography using a toluene/ethyl acetate mixture (98/2 v/v) as the eluent.

$n_D^{25°\ C.} = 1.5182$

PREPARATION LI

Preparation of 2-trifluoromethylbenzenethiol

If the procedure described in Preparation XIII is followed starting from 2.72 g ($10.9.10^{-3}$ mol) of S-2-trifluoromethylphenyl dimethylthiocarbamate, 2 g (quantitative yield) of the expected product are obtained.

PREPARATION LII

Preparation of 2-trifluoromethylphenyl 2,3,4-tri-O-acetyl-1,5-dithio-β-D-xylopyranoside (Example 13a)

If the procedure described in Preparation I is followed starting from 1.8 g ($10.10^{-3}$ mol) of 2-trifluoromethylbenzenethiol, 2.55 g ($10.10^{-3}$ mol) of mercuric cyanide ($Hg(CN)_2$) and 3.95 g ($11.10^{-3}$ mol) of 2,3,4-tri-O-acetyl-5-thio-α-D-xylopyranosyl bromide, 1.53 g (yield: 34%) of the expected product are obtained.

M.p. = 152° C.
$[\alpha]_D^{20°\ C.} = +64°$ (c = 0.5; CH$_3$OH)

PREPARATION LIII

Preparation of 2-trifluoromethylphenyl 1,5-dithio-β-D-xylopyranoside (Example 13)

If the procedure described in Preparation V is followed starting from 1.38 g (3.10$^{-3}$ mol) of 2-trifluoromethylphenyl 2,3,4-tri-O-acetyl-1,5-dithio-β-D-xylopyranoside (Example 13a), 0.75 g (yield: 75%) of the expected product is obtained after recrystallization from a methanol/water mixture (1/1 v/v).

M.p. = 114°–115° C.
$[\alpha]_D^{20°\ C.} = +34°$ (c = 0.5; CH$_3$OH)

PREPARATION LIV

Preparation of 4-(4-iodophenyl)benzonitrile

A mixture of 15 g (33.2.10$^{-3}$ mol) of 4,4'-diiodo-1,1'-biphenyl, 3.13 g (34.9.10$^{-3}$ mol) of mercuric cyanide and 2.75 g (34.9.10$^{-3}$ mol) of pyridine is heated at 200° C. for 15 minutes and 6 ml of dimethylformamide are then added to the mixture. After cooling, the reaction medium is hydrolyzed with a 1N aqueous solution of hydrochloric acid. The expected product is extracted with ethyl acetate. The organic phase obtained is washed with water until the pH of the washings is neutral, dried over magnesium sulfate and evaporated under vacuum. 3.28 g (yield: 33%) of a yellow solid are obtained after purification by flash chromatography using a chloroform/toluene mixture (1/1 v/v) as the eluent.

M.p. = 162°–168° C.

PREPARATION LV

Preparation of 4-(4-mercaptophenyl)benzonitrile 3.25 g (10.8.10$^{-3}$ mol) of 4-(4-iodophenyl)benzonitrile are dissolved in 50 ml of hexamethylphosphoramide, and 3.05 g (43.4.10$^{-3}$ mol) of sodium thiomethylate are then added to the solution. The reaction mixture is heated at 100° C. for 1.5 hours and then, after cooling, hydrolyzed in a 1N hydrochloric acid/ice mixture. The expected product is extracted with ethyl acetate. The resulting organic phase is washed with water until the pH of the washings is neutral, dried over magnesium sulfate and then evaporated under reduced pressure to give 2.4 g (quantitative yield) of a pale yellow solid.

M.p. = 105°–115° C.

PREPARATION LVI

Preparation of 4-(4-cyanophenyl)phenyl 2,3,4-tri-O-acetyl-1,5-dithio-β-D-xylopyranoside (Example 14a)

If the procedure described in Preparation I is followed starting from 2.3 g (10.9.10$^{-3}$ mol) of 4-(4-mercaptophenyl)benzonitrile, 4.26 g (11.9.10$^{-3}$ mol) of 2,3,4-tri-O-acetyl-5-thio-α-D-xylopyranosyl bromide and 2.75 g (10.9.10$^{-3}$ mol) of mercuric cyanide (Hg(CN)$_2$), 0.540 g (yield: 10%) of the expected product is obtained after purification by flash chromatography using methylene chloride as the eluent.

M.p. = 150° C.
$[\alpha]_D^{20°\ C.} = +10.2°$ (c = 0.5; CHCl$_3$)

PREPARATION LVII

Preparation of 4-(4-cyanophenyl)phenyl 1,5-dithio-β-D-xylopyranoside (Example 14)

If the procedure described in Preparation V is followed starting from 0.340 g (70.1.10$^{-3}$ mol) of 4-(4-cyanophenyl)phenyl 2,3,4-tri-O-acetyl-1,5-dithio-β-D-xylopyranoside (Example 14a) and 17 ml of sodium methylate (8% w/v solution of Na in methanol), 0.200 g (yield: 80%) of the expected product is obtained after purification by recrystallization from methanol.

M.p. = 168° C.
$[\alpha]_D^{20°\ C.} = +5.4°$ (c = 0.5; CH$_3$OH/CH$_3$Cl (1/1 v/v))

PREPARATION LVIII

Preparation of O-3,5-bis(trifluoromethyl)phenyl dimethylthiocarbamate 0.975 g (17.4.10$^{-3}$ mol) of potassium hydroxide pellets is dissolved in 60 ml of water, 3.81 g (16.5.10$^{-3}$ mol) of 3,5-bis(trifluoromethyl)benzenethiol are then added and the mixture obtained is stirred for 20 minutes at room temperature. A solution of 2.35 g (19.10$^{-3}$ mol) of dimethylthiocarbamoyl chloride in 60 ml of acetone is then added dropwise, after which the resulting solution is stirred for 30 minutes at room temperature. The reaction medium is hydrolyzed in a mixture of ice and 1N hydrochloric acid and then extracted with ethyl acetate. The organic phase is washed with water until the pH of the washings is neutral, dried over magnesium sulfate, decolorized with animal charcoal and evaporated under reduced pressure to give 4.81 g of the expected product (yield: 92%) in the form of a pale yellow solid.

M.p. = 71°–80° C.

PREPARATION LIX

Preparation of S-3,5-bis(trifluoromethyl)phenyl dimethylthiocarbamate 4.81 g (15.10$^{-3}$ mol) of O-3,5-bis(trifluoromethyl)phenyl dimethylthiocarbamate are heated at 200°–210° C. for 2 hours to give 2.81 g (yield: 58.4%) of the expected product in the form of a yellow oil.

$n_D^{25°\ C.} = 1.4710$

PREPARATION LX

Preparation of 3,5-bis(trifluoromethyl)benzenethiol 2.25 g (7.1.10$^{-3}$ mol) of S-3,5-bis(trifluoromethyl)phenyl dimethylthiocarbamate are dissolved in 2.2 ml of anhydrous dimethylformamide. The resulting solution is cooled to 0° C. before the addition of 4 ml (14.10$^{-3}$ mol) of sodium methylate dissolved in methanol, and is then stirred at 0° C. for 10 minutes. The reaction medium is subsequently hydrolyzed with an ice/water/1N HCl mixture and then extracted with methylene chloride. The organic phase obtained is washed with a saturated solution of sodium chloride, dried over magnesium sulfate and evaporated under reduced pressure to give 1.74 g (yield: 100%) of the expected product in the form of a yellow oil, which crystallizes and dimerizes under the action of heat.

Melting point of the dimer = 71° C.

PREPARATION LXI

Preparation of 3,5-bis(trifluoromethyl)phenyl 2,3,4-tri-O-acetyl-1,5-dithio-β-D-xylopyranoside (Example 15a)

If the procedure described in Preparation I is followed starting from 1.6 g ($6.5.10^{-3}$ mol) of 3,5-bis(trifluoromethyl)benzenethiol, 1.64 g ($6.5.10^{-3}$ mol) of mercuric cyanide, $Hg(CN)_2$, and 2.54 g ($7.5.10^{-3}$ mol) of 2,3,4-tri-O-acetyl-5-thio-α-D-xylopyranosyl bromide, 1.2 g (yield: 35.7%) of the expected product are obtained.

M.p.=201° C.
$[\alpha]D^{20°}$ C.=+6° (c=0.5; $CHCl_3$)

PREPARATION LXII

Preparation of 3,5-bis(trifluoromethyl)phenyl 1,5-dithio-β-D-xylopyranoside (Example 15)

If the procedure described in Preparation V is followed starting from 1.1 g ($2.1.10^{-3}$ mol) of 3,5-bis(trifluoromethyl)phenyl 2,3,4-tri-O-acetyl-1,5-dithio-β-D-xylopyranoside, 0.600 g (yield: 72%) of the expected product is obtained after recrystallization from a methanol/water mixture (1/1 v/v).

M.p.=157°-158° C.
$[\alpha]D^{20°}$ C.=+3° (c=0.5; $CH_3OH$)

PREPARATION LXIII

Preparation of 3-cyano-4-mercaptobenzonitrile

Under argon, 3.03 g ($12.10^{-3}$ mol) of 3-cyano-4-iodobenzonitrile and 3.36 g ($48.10^{-3}$ mol) of sodium thiomethylate are dissolved in 80 ml of anhydrous hexamethylphosphoramide and the solution obtained is then heated at 80° C. for 45 minutes. The resulting reaction medium is hydrolyzed in an ice/1N HCl mixture and then extracted with methylene chloride. The organic phase is washed with water and then dried over magnesium sulfate and evaporated under reduced pressure to give 1.55 g (yield: 81%) of the expected product.

M.p.=180° C.

PREPARATION LXIV

Preparation of 2,4-dicyanophenyl 2,3,4-tri-O-acetyl-1,5-dithio-β-D-xylopyranoside (Example 16a)

If the procedure described in Preparation I is followed starting from 1.5 g ($9.10^{-3}$ mol) of 3-cyano-4-mercaptobenzonitrile, 2.78 g ($11.10^{-3}$ mol) of mercuric cyanide, $Hg(CN)_2$, and 3.66 g ($11.10^{-3}$ mol) of 2,3,4-tri-O-acetyl-5-thio-α-D-xylopyranosyl bromide, 1.65 g (yield: 40.5%) of the expected product are obtained.

M.p.=228° C.
$[\alpha]D^{20°}$ C.=−14° (c=0.39; $CHCl_3$)

PREPARATION LXV

Preparation of 2,4-dicyanophenyl 2,3,4-tri-O-acetyl-1,5-dithio-β-D-xylopyranoside (Example 16a)

If the procedure described in Preparation IV is followed starting from 1.6 g ($9.73.10^{-3}$ mol) of 3-cyano-4-mercaptobenzonitrile, 4.07 g ($11.45.10^{-3}$ mol) of 2,3,4-tri-O-acetyl-5-thio-α-D-xylopyranosyl bromide and 0.84 g ($10.10^{-3}$ mol) of zinc oxide (ZnO), 2.08 g (yield: 47%) of the expected product are obtained.

M.p.=228° C.

PREPARATION LXVI

Preparation of 2,4-dicyanophenyl 1,5-dithio-β-D-xylopyranoside (Example 16)

If the procedure described in Preparation V is followed, except that the reaction is carried out at 0° C., starting from 1.5 g ($34.10^{-3}$ mol) of 2,4-dicyanophenyl 2,3,4-tri-O-acetyl-1,5-dithio-β-D-xylopyranoside (Example 16a), 0.71 g (yield: 67%) of the expected product is obtained after chromatography on silica using a $CH_2Cl_2/CH_3OH$ mixture (8/1 v/v) as the eluent.

M.p.=180°-181° C.
$[\alpha]D^{20°}$ C.=+42.7° (c=0.48; $CH_3OH$)

PREPARATION LXVII

Preparation of 3,5-dicyano-2-mercaptobenzonitrile

If the procedure described in Preparation LV is followed starting from 6 g ($26.10^{-3}$ mol) of 2-bromo-3,5-dicyanobenzonitrile and 6 g ($86.10^{-3}$ mol) of sodium thiomethylate, 6 g (quantitative yield) of the expected product are obtained in the form of an oil.

$nD^{29.5°}$ C.=1.5012

PREPARATION LXVIII

Preparation of 2,4,6-tricyanophenyl 2,3,4-tri-O-acetyl-1,5-dithio-β-D-xylopyranoside (Example 17a)

If the procedure described in Preparation I is followed starting from 4.8 g ($258.10^{-3}$ mol) of 3,5-dicyano-2-mercaptobenzonitrile (Example 17a), 9.71 g ($258.10^{-3}$ mol) of 2,3,4-tri-O-acetyl-5-thio-α-D-xylopyranosyl bromide and 6.57 g ($8.6.10^{-3}$ mol) of mercuric cyanide ($Hg(CN)_2$), 2 g (yield: 17%) of the expected product are obtained after crystallization from ether.

M.p.=221° C.
$[\alpha]D^{20°}$ C.=+84.6° (c=0.325; $CHCl_3$)

PREPARATION LXIX

Preparation of 2,4,6-tricyanophenyl 1,5-dithio-β-D-xylopyranoside (Example 17)

0.600 g ($1.30.10^{-3}$ mol) of 2,4,5-tricyanophenyl 2,3,4-tri-O-acetyl-1,5-dithio-β-D-xylopyranoside is suspended in 120 ml of 0.1M $Na_2HPO_4/NaH_2PO_4$ buffer (pH: 7.35) and 3 drops of Triton ® X100 (marketed by SIGMA). 30 drops of pork liver esterase [Sigma type I, 3.2M suspension in $(NH_4)_2SO_4$] (marketed by SIGMA) are then added and the resulting mixture is stirred at 30°-35° C. for 12 hours. A further 20 drops of pork liver esterase and 10 drops of Triton ® X100 are added; finally, after stirring for 24 hours, 30 drops of pork liver esterase are added. The pH is kept at 7.4 by the addition of 1N sodium hydroxide solution throughout the experiment. After stirring for 84 hours, the reaction mixture is cooled and the expected product is extracted with ethyl acetate. The resulting organic phase is washed with brine and then dried over magnesium sulfate and evaporated under reduced pressure. 100 mg (yield: 23%) of the expected product are obtained in the form of a foam after purification by flash chromatography using a $CHCl_3/CH_3OH$ mixture (98/2 v/v, then 95/5 v/v) as the eluent. It is a hydrated product containing 1.3 $H_2O$ per molecule.

M.p.=86°-96° C.
$[\alpha]D^{20°}$ C.=0° (c=0.165; $CH_3OH$)

PREPARATION LXX

Preparation of 4-aminophenyl 1,5-dithio-β-D-xylopyranoside (Example 18)

170 mg of 10% palladium-on-charcoal are added to a solution of 1.7 g ($5.61.10^{-3}$ mol) of 4-nitrophenyl 1,5-dithio-β-D-xylopyranoside in 150 ml of methanol. The reaction medium is kept under hydrogen pressure ($3.5.10^5$ Pa) at room temperature for 3 days. Repeat amounts of 170 mg of 10% palladium-on-charcoal are added after stirring for 3 hours, 4 hours, 12 hours and 24 hours. The mixture obtained is filtered, the solvent is evaporated off under reduced pressure and the residue obtained is purified by flash chromatography using a CHCl$_3$/CH$_3$OH mixture (9/1 v/v) as the eluent, and is then recrystallized from water to give 0.7 g (yield: 46%) of the expected product.

M.p.=163°–166° C.
[α]$D^{23°}$ C.=−74° (c=0.102; DMSO)

PREPARATION LXXI

Preparation of 4-acetamidophenyl 2,3,4-tri-O-acetyl-1,5dithio-β-D-xylopyranoside (Example 19a)

If the procedure described in Preparation IV is followed starting from 4.5 g ($27.10^{-3}$ mol) of N-(4-mercaptophenyl)acetamide, 11.43 g ($32.10^{-3}$ mol) of 2,3,4-tri-O-acetyl-5-thio-D-xylopyranosyl bromide and 2.16 g ($27.10^{-3}$ mol) of zinc oxide (ZnO), 3 g (yield: 25%) of the expected product are obtained after recrystallization from a toluene/isopropyl ether mixture.

M.p.=168°–174° C.
[α]$D^{23°}$ C.=+8° (c=0.5; CHCl$_3$)

PREPARATION LXXII

Preparation of 4-acetamidophenyl 1,5-dithio-β-D-xylopyranoside (Example 19)

If the procedure described in Preparation V is followed starting from 1.05 g ($2.38.10^{-3}$ mol) of 4-acetamidophenyl 2,3,4-tri-O-acetyl-1,5-dithio-β-D-xylopyranoside (Example 19a), 0.61 g (yield: 81%) of the expected product is obtained after recrystallization from 70 ml of water.

M.p.=226°–233° C.
[α]$D^{23°}$ C.=−25.25° (c=0.59; DMSO)

PREPARATION LXXIII

Preparation of 4-trifluoroacetylphenyl 2,3,4-tri-O-acetyl-1,5-dithio-β-D-xylopyranoside (Example 20a)

If the procedure described in Preparation I is followed starting from 9.03 g ($43.8.10^{-3}$ mol) of 2,2,2-trifluoro-1-(4-mercaptophenyl)ethanone, 11.5 g ($45.5.10^{-3}$ mol) of mercuric cyanide and 17.1 g ($48.2.10^{-3}$ mol) of 2,3,4-tri-O-acetyl-1-bromo-5-thio-D-xylopyranoside, 4.79 g (yield: 22%) of the expected product are obtained after purification by flash chromatography using a toluene/ether mixture (8/2 v/v) as the eluent, and recrystallization from ether.

M.p.=143°–148° C.
[α]$D^{24°}$ C.=+59.3° (c=0.28; CHCl$_3$)

PREPARATION LXXIV

Preparation of 4-trifluoroacetylphenyl 1,5-dithio-β-D-xylopyranoside (Example 20)

If the procedure described in Preparation V is followed starting from 3.65 g ($7.6.10^{-3}$ mol) of 4-trifluoroacetylphenyl 2,3,4-tri-O-acetyl-1,5-dithio-β-D-xylopyranoside (Example 20a), 1.4 g (yield: 52%) of the expected product are obtained after purification by recrystallization from a toluene/n-propyl alcohol/hexane mixture.

M.p.=133°–134° C.
[α]$D^{22°}$ C.=+15° (c=0.31; CH$_3$OH)

PREPARATION LXXV

Preparation of 3-aminophenyl 1,5-dithio-β-D-xylopyranoside (Example 21)

If the procedure described in Preparation LXX is followed starting from 2.9 g ($9.6.10^{-3}$ mol) of 3-nitrophenyl 1,5-dithio-β-D-xylopyranoside, 1.2 g (yield: 46%) of the expected product are obtained after purification by flash chromatography using a CHCl$_3$/CH$_3$OH mixture as the eluent (solvent proportions from 95/5 to 92/8 v/v), and precipitation in a CH$_3$OH/ether mixture.

M.p.=128°–132° C.
[α]$D^{25°}$ C.=+3.5° (c=0.31; CH$_3$OH)

PREPARATION LXXVI

Preparation of 4-cyanophenyl 2,3,4-tri-O-acetyl-5-thio-β-D-xylopyranoside (Example 22a)

A suspension of 6.5 g ($12.3.10^{-3}$ mol) of 2,3,4-tri-O-acetyl-5-thio-α-D-xylopyranosyl bromide, 6 g ($50.4.10^{-3}$ mol) of 4-hydroxybenzonitrile, 6.9 g ($50.5.10^{-3}$ mol) of zinc chloride and 4.4 g ($25.1.10^{-3}$ mol) of silver imidazolate in 200 ml of anhydrous methylene chloride is stirred at 40° C., under an inert atmosphere, in the absence of light and in the presence of a molecular sieve (400 pm). After 7 h at this temperature, 6.9 g ($50.5.10^{-3}$ mol) of zinc chloride, 4.4 g ($25.1.10^{-3}$ mol) of silver imidazolate and 6.5 g ($18.3.10^{-3}$ mol) of 2,3,4-tri-O-acetyl-5-thio-α-D-xylopyranosyl bromide are added. The reaction medium is left overnight under these conditions and 6.5 g ($12.3.10^{-3}$ mol) of 2,3,4-tri-O-acetyl-5-thio-α-D-xylopyranosyl bromide are then added. After 24 h, the reaction mixture is filtered on Célite ®, washed with a 1N aqueous solution of hydrochloric acid and then water and dried over magnesium sulfate. After evaporation under reduced pressure, the residue is purified by chromatography on silica gel using a hexane/ethyl acetate mixture (3/1 v/v) as the eluent. 8.1 g (yield: 41%) of the expected product are obtained by crystallization from ethanol.

M.p.=145°–148° C.
[α]$D^{21°}$ C.=−29° (c=0.47; CHCl$_3$)

PREPARATION LXXVII

Preparation of 2,3,4-tri-O-acetyl-5-thio-β-D-xylopyranosyl bromide 3.50 ml of a 30% solution of hydrobromic acid in glacial acetic acid are added at 10° C. to a solution of 2.10 g ($6.3.10^{-3}$ mol) of 1,2,3,4-tetra-O-acetyl-5-thio-D-xylopyranose in 10 cm$^3$ of dichloroethane. After 2 to 3 h, the reaction medium is hydrolyzed, washed with a solution of sodium bicarbonate and dried over sodium sulfate (Na$_2$SO$_4$) and the solvent is evaporated off to dryness under reduced pressure. 0.87 g (yield: 39%) of the expected product is obtained after precipitation in ether.

M.p. = 175° C.
[α]$D^{21°}$ $^{C.}$ = −67° (c=0.56; CHCl$_3$)

PREPARATION LXXVIII

Preparation of 4-cyanophenyl 2,3,4-tri-O-acetyl-5-thio-β-D-xylopyranoside (Example 22a)

A suspension of 0.5 g (1.4.10$^{-3}$ mol) of 2,3,4-tri-O-acetyl-5-thio-D-xylopyranosyl bromide, 0.25 g (2.1.10$^{-3}$ mol) of 4-hydroxybenzonitrile and 170 mg (2.1.10$^{-3}$ mol) of zinc oxide (ZnO) in 4 ml of anhydrous toluene and 4 ml of acetonitrile is stirred at 50° C., under an inert atmosphere, in the presence of a molecular sieve (1 nm), for 48 h. The reaction medium is subsequently filtered on Célite ® in ethyl acetate and then washed with a 1N aqueous solution of hydrochloric acid, water, a 1N solution of sodium hydroxide and then a saturated solution of NaCl. The solution obtained is dried over sodium sulfate and the solvent is evaporated off under reduced pressure. The residue obtained is purified by chromatography on silica gel using a hexane/ethyl acetate mixture (2/1 v/v) as the eluent to give 194 mg (yield: 35%) of the expected product.

M.p. = 145°-148° C.

PREPARATION LXXIX

Preparation of 2,3,4-tri-O-acetyl-5-thio-α-D-xylopyranose 22 ml (0.2 mol) of benzylamine are added under an inert atmosphere to a solution of 15 g (44.8.10$^{-3}$ mol) of 1,2,3,4-tetra-O-acetyl-5-thio-D-xylopyranose in 450 ml of ether. After 7 hours at room temperature (15°-25° C.), the reaction mixture is concentrated under reduced pressure and the residue is dissolved in methylene chloride and washed with a 1N solution of hydrochloric acid, a saturated solution of ammonium chloride and then water. The solution obtained is dried over sodium sulfate and the solvent is evaporated off under reduced pressure. 6.2 g (yield: 47%) of the expected product are obtained after purification by chromatography on silica gel using a hexane/ethyl acetate mixture (3/2 v/v) as the eluent, and crystallization from an ethyl acetate/hexane mixture, said product having the following physical characteristics:

M.p. = 115° C.
[α]$D^{21°}$ $^{C.}$ = +131° (c=0.34; CHCl$_3$)

PREPARATION LXXX

Preparation of 2,3,4-tri-O-acetyl-5-thio-α-D-xylopyranosyl trichloroacetimidate 1.5 ml (15.10$^{-3}$ mol) of trichloroacetonitrile and 70 mg of NaH (2.3.10$^{-3}$ mol of NaH in 80% dispersion) are added to a solution of 1 g (3.42.10$^{-3}$ mol) of 2,3,4-tri-O-acetyl-5-thio-α-D-xylopyranose in 10 ml of methylene chloride. After 4 h at room temperature, the reaction medium is filtered on silica in methylene chloride and then purified by chromatography on silica gel using a hexane/ethyl acetate mixture (3/1 v/v) as the eluent. 790 mg (yield: 53%) of the expected product are obtained after crystallization from an ethyl acetate/hexane mixture.

M.p. = 110° C.
[α]$D^{21°}$ $^{C.}$ = +227° C. (c=0.42; CHCl$_3$)

PREPARATION LXXXI

Preparation of 4-cyanophenyl 2,3,4-tri-O-acetyl-5-thio-β-D-xylopyranoside (Example 22a)

1 ml of a 0.1M solution of boron trifluoride etherate in methylene chloride is added at −15° C., under an inert atmosphere, to a suspension of 250 mg (0.57.10$^{-3}$ mol) of 2,3,4-tri-O-acetyl-5-thio-α-D-xylopyranosyl trichloroacetimidate, 57 mg (0.48.10$^{-3}$ mol) of 4-hydroxybenzonitrile and a molecular sieve (1 nm) in 10 ml of methylene chloride. The reaction medium is allowed to return gradually to 0° C. and, after a reaction time of 3 h, is neutralized with sodium bicarbonate. The reaction mixture is then washed with water and dried over magnesium sulfate, MgSO$_4$, and the solvent is evaporated off under reduced pressure. 150 mg (yield: 80%) of the expected product are obtained after purification by chromatography on silica gel using a hexane/ethyl acetate mixture (2/1 v/v) as the eluent.

M.p. = 145°-148° C.

PREPARATION LXXXII

Preparation of 4-cyanophenyl 5-thio-β-D-xylopyranoside (Example 22)

1.5 ml of a solution of sodium methylate in methanol (8% w/v of Na) are added under an inert atmosphere to a suspension of 10 g (25.4.10$^{-3}$) of 4-cyanophenyl 2,3,4-tri-O-acetyl-5-thio-β-D-xylopyranoside in 200 ml of methanol. The reaction mixture is stirred at room temperature for 30 min, neutralized by the addition of Amberlite ® IR 120 H$^+$ resin and filtered. After evaporation to dryness, the residue is crystallized from methanol to give 8.8 g (yield: 73%) of the expected product.

M.p. = 179°-186° C.
[α]$D^{21°}$ $^{C.}$ = −108.6° (c=0.48; CH$_3$OH)

PREPARATION LXXXIII

Preparation of 4-nitrophenyl 2,3,4-tri-O-acetyl-5-thio-β-D-xylopyranoside (Example 23a)

A suspension of 5.6 g (15.8.10$^{-3}$ mol) of 2,3,4-tri-O-acetyl-5-thio-α-D-xylopyranosyl bromide, 2 g (14.3.10$^{-3}$ mol) of 4-nitrophenol, 4 g (29.3.10$^{-3}$ mol) of zinc chloride and 3.8 g (21.7.10$^{-3}$ mol) of silver imidazolate in 80 ml of anhydrous methylene chloride is stirred at 50° C., under an inert atmosphere, in the absence of light and in the presence of a molecular sieve (400 pm). After 48 h at this temperature, the reaction mixture is filtered on Célite ®, washed with a 1N aqueous solution of hydrochloric acid, then a 1N solution of sodium hydroxide and finally water and dried over magnesium sulfate (MgSO$_4$). After evaporation to dryness, the residue is purified by chromatography on silica gel using a hexane/ethyl acetate mixture (3/1 v/v) as the eluent. 1.5 g (yield: 25%) of the expected product are obtained by precipitation in ether.

M.p. = 212° C.
[α]$D^{21°}$ $^{C.}$ = −78° (c=0.5; CHCl$_3$)

PREPARATION LXXXIV

Preparation of 4-nitrophenyl
5-thio-β-D-xylopyranoside (Example 23)

0.2 ml of a solution of sodium methylate in methanol (8% w/v of Na) is added under an inert atmosphere to a suspension of 1.1 g ($2.6.10^{-3}$ mol) of 4-nitrophenyl 2,3,4-tri-O-acetyl-5-thio-β-D-xylopyranoside in 30 ml of methanol. After complete solubilization (2 h), the reaction mixture is neutralized by the addition of Amberlite® IR 120 H+ resin and then filtered. 620 mg (yield: 79%) of the expected product are obtained after evaporation to dryness and lyophilization.

M.p.=130°-132° C.
$[\alpha]D^{21°\ C.} = -77.3°$ (c=0.49; CH$_3$OH)

PREPARATION LXXXV

Preparation of 4-acetylphenyl
2,3,4-tri-O-acetyl-5-thio-β-D-xylopyranoside (Example 24a)

If the procedure described in Preparation LXXXIII is followed starting from 2 g ($14.7.10^{-3}$ mol) of 1-(4-hydroxyphenyl)ethanone, 2.8 g ($16.10^{-3}$ mol) of silver imidazolate, 5.74 g ($16.1.10^{-3}$ mol) of 2,3,4-tri-O-acetyl-5-thio-α-D-xylopyranosyl bromide and 4 g ($29.3.10^{-3}$ mol) of zinc chloride in 100 ml of methylene chloride, 0.96 g (yield: 18%) of the expected product is obtained after purification by chromatography on silica gel using a toluene/ethyl acetate mixture (6/1 v/v) as the eluent.

M.p.=156° C.
$[\alpha]D^{21°\ C.} = -77°$ (c=0.5; CHCl$_3$)

PREPARATION LXXXVI

Preparation of 4-acetylphenyl
2,3,4-tri-O-acetyl-5-thio-β-D-xylopyranoside (Example 24a)

If the procedure described in Preparation LXXXI is followed starting from 380 mg ($0.882.10^{-3}$ mol) of 2,3,4-tri-O-acetyl-5-thio-α-D-xylopyranosyl trichloroacetimidate, 100 mg ($73.5.10^{-3}$ mol) of 1-(4-hydroxyphenyl)ethanone and 1.47 ml of a 0.1M solution of boron trifluoride etherate in methylene chloride, 140 mg (yield: 47%) of the expected product are obtained after crystallization from ether.

M.p.=156° C.

PREPARATION LXXXVII

Preparation of 4-acetylphenyl
5-thio-β-D-xylopyranoside (Example 24)

If the procedure described in Preparation LXXXIV is followed starting from 0.9 g ($2.2.10^{-3}$ mol) of 4-acetylphenyl 2,3,4-tri-O-acetyl-5-thio-β-D-xylopyranoside and 0.8 ml of a solution of sodium methylate in methanol (8% w/v of Na), reacted in 50 ml of methanol for 1 h, 0.55 g (yield: 88%) of the expected product is obtained after lyophilization.

M.p.=195°-198° C.
$[\alpha]D^{21°\ C.} = -84.5°$ (c=0.49; CH$_3$OH)

PREPARATION LXXXVIII

Preparation of 3-acetylphenyl
2,3,4-tri-O-acetyl-5-thio-β-D-xylopyranoside (Example 25a)

If the procedure described in Preparation LXXXIII is followed starting from 3.45 g ($25.3.10^{-3}$ mol) of 1-(3-hydroxyphenyl)ethanone, 6 g ($16.9.10^{-3}$ mol) of 2,3,4-tri-O-acetyl-5-thio-D-xylopyranosyl bromide, 3 g ($17.10^{-3}$ mol) of silver imidazolate and 4.6 g ($33.7.10^{-3}$ mol) of zinc chloride in 90 ml of methylene chloride and 30 ml of acetonitrile, 0.96 g (yield: 14%) of the expected product is obtained after purification by chromatography on silica gel using a toluene/ethyl acetate mixture (6/1 v/v) as the eluent, and crystallization from ether.

M.p.=150°-153° C.
$[\alpha]D^{21°\ C.} = -81.5°$ (c=0.5; CHCl$_3$)

PREPARATION LXXXIX

Preparation of 3-acetylphenyl
5-thio-β-D-xylopyranoside (Example 25)

If the procedure described in Preparation LXXXIV is followed starting from 1.36 g ($3.3.10^{-3}$ mol) of 3-acetylphenyl 2,3,4-tri-O-acetyl-5-thio-β-D-xylopyranoside and 0.2 ml of a solution of sodium methylate in methanol (8% w/v of Na), reacted in 50 ml of methanol for 30 min, 0.8 g (yield: 85%) of the expected product is obtained after crystallization from an ethanol/ether mixture.

M.p.=166°-174° C.
$[\alpha]D^{21°\ C.} = -109°$ (c=0.42; CH$_3$OH)

PREPARATION XC

Preparation of 2-cyanophenyl
2,3,4-tri-O-acetyl-5-thio-β-D-xylopyranoside (Example 26a)

If the procedure described in Preparation LXXXIII is followed starting from 2 g ($16.8.10^{-3}$ mol) of 2-hydroxybenzonitrile, 4.4 g ($25.1.10^{-3}$ mol) of silver imidazolate, 6.5 g ($18.3.10^{-3}$ mol) of 2,3,4-tri-O-acetyl-5-thio-α-D-xylopyranosyl bromide and 4.6 g ($33.6.10^{-3}$ mol) of zinc chloride in 80 ml of methylene chloride, 1.32 g (yield: 20%) of the expected product are obtained after purification by chromatography on silica gel using a toluene/ethyl acetate mixture (6/1 v/v) as the eluent, and precipitation in ether.

M.p.=176° C.
$[\alpha]D^{21°\ C.} = -160°$ (c=0.45; CHCl$_3$)

PREPARATION XCI

Preparation of 2-cyanophenyl
5-thio-β-D-xylopyranoside (Example 26)

If the procedure described in Preparation LXXXIV is followed starting from 1.26 g ($3.2.10^{-3}$ mol) of 2-cyanophenyl 2,3,4-tri-O-acetyl-5-thio-β-D-xylopyranoside and 0.2 ml of a solution of sodium methylate in methanol (8% w/v of Na), reacted in 70 ml of methanol for 30 min, 0.75 g (yield: 88%) of the expected product is obtained after precipitation in ether and lyophilization.

M.p.=130°-132° C.
$[\alpha]D^{21°\ C.} = -68.8°$ (c=0.485; CH$_3$OH)

PREPARATION XCII

Preparation of 3-cyanophenyl
2,3,4-tri-O-acetyl-5-thio-β-D-xylopyranoside (Example 27a)

If the procedure described in Preparation LXXXIII is followed starting from 2 g ($16.8.10^{-3}$ mol) of 3-hydroxybenzonitrile, 2.9 mg ($16.5.10^{-3}$ mol) of silver imidazolate, 6.5 g ($18.3.10^{-3}$ mol) of 2,3,4-tri-O-acetyl-5-thio-α-D-xylopyranosyl bromide and 4.6 g ($33.6.10^{-3}$ mol) of zinc chloride in 80 ml of methylene chloride, 2.2 g (yield: 33%) of the expected product are obtained after purification by chromatography on silica gel using a hexane/ethyl acetate mixture (3/1 v/v) as the eluent, and precipitation in ether.
M.p.=148°-151° C.
$[\alpha]D^{21°\ C.} = -82°$ (c=0.31; CHCl$_3$)

PREPARATION XCIII

Preparation of 3-cyanophenyl 2,3,4-tri-O-acetyl-5-thio-β-D-xylopyranoside (Example 27a)

If the procedure described in Preparation LXXVIII is followed starting from 0.5 g (1.4.10$^{-3}$ mol) of 2,3,4-tri-O-acetyl-5-thio-D-xylopyranosyl bromide, 0.25 g (2.1.10$^{-3}$ mol) of 3-hydroxybenzonitrile and 170 mg (2.1.10$^{-3}$ mol) of zinc oxide (ZnO) in 4 ml of anhydrous toluene and 4 ml of acetonitrile, 138 mg (yield: 25%) of the expected product are obtained after purification by chromatography on silica gel using a hexane/ethyl acetate mixture (2/1 v/v) as the eluent, and precipitation in ether.
M.p.=148°-151° C.

PREPARATION XCIV

Preparation of 3-cyanophenyl 5-thio-β-D-xylopyranoside (Example 27)

If the procedure described in Preparation LXXXIV is followed starting from 2.12 g (5.4.10$^{-3}$ mol) of 3-cyanophenyl 2,3,4-tri-O-acetyl-5-thio-β-D-xylopyranoside and 0.2 ml of a solution of sodium methylate in methanol (8% w/v of Na), reacted in 60 ml of methanol for 30 min, 1.22 g (yield: 85%) of the expected product are obtained after precipitation in ether and lyophilization.
M.p.=130°-135° C.
$[\alpha]D^{21°\ C.} = -107.4°$ (c=0.47; CH$_3$OH)

PREPARATION XCV

Preparation of 2-nitrophenyl 2,3,4-tri-O-acetyl-5-thio-β-D-xylopyranoside (Example 28a)

If the procedure described in Preparation LXXXIII is followed starting from 2 g (14.4.10$^{-3}$ mol) of 2-nitrophenol, 2.5 g (14.2.10$^{-3}$ mol) of silver imidazolate, 6 g (15.7.10$^{-3}$ mol) of 2,3,4-tri-O-acetyl-5-thio-α-D-xylopyranosyl bromide and 4 g (29.3.10$^{-3}$ mol) of zinc chloride in 80 ml of methylene chloride, 0.91 g (yield: 15%) of the expected product is obtained after purification by chromatography on silica gel using a hexane/ethyl acetate mixture (2/1 v/v) as the eluent, and precipitation in ether.
M.p.=148° C.
$[\alpha]D^{21°\ C.} = -102.8°$ (c=0.40; CHCl$_3$)

PREPARATION XCVI

Preparation of 2-nitrophenyl 5-thio-β-D-xylopyranoside (Example 28)

If the procedure described in Preparation LXXXIV is followed starting from 0.85 g (2.05.10$^{-3}$ mol) of 2-nitrophenyl 2,3,4-tri-O-acetyl-5-thio-β-D-xylopyranoside and 0.1 ml of a solution of sodium methylate in methanol (8% w/v of Na), reacted in 50 ml of methanol for 30 min, 0.4 g (yield: 68%) of the expected product is obtained after precipitation in ether and lyophilization.
M.p.=137°-140° C.
$[\alpha]D^{21°\ C.} = -117°$ (c=0.35; CH$_3$OH)

PREPARATION XCVII

Preparation of 2-acetylphenyl 2,3,4-tri-O-acetyl-5-thio-β-D-xylopyranoside (Example 29a)

If the procedure described in Preparation LXXXIII is followed starting from 3.45 g (25.3.10$^{-3}$ mol) of 1-(2-hydroxyphenyl)ethanone, 6 g (16.9.10$^{-3}$ mol) of 2,3,4-tri-O-acetyl-5-thio-D-xylopyranosyl bromide, 3 g (17.10$^{-3}$ mol) of silver imidazolate and 4.6 g (33.7.10$^{-3}$ mol) of zinc chloride in 90 ml of methylene chloride and 30 ml of acetonitrile, 0.92 g (yield: 13.5%) of the expected product is obtained after purification by chromatography on silica gel using a toluene/ethyl acetate mixture (6/1 v/v) as the eluent, and crystallization from ether.
M.p.=112° C.
$[\alpha]D^{21°\ C.} = -100°$ (c=0.42; CHCl$_3$)

PREPARATION XCVIII

Preparation of 2-acetylphenyl 5-thio-β-D-xylopyranoside (Example 29)

If the procedure described in Preparation LXXXIV is followed starting from 0.88 g (2.1.10$^{-3}$ mol) of 2-acetylphenyl 2,3,4-tri-O-acetyl-5-thio-β-D-xylopyranoside and 0.1 ml of a solution of sodium methylate in methanol (8% w/v of Na), reacted in 50 ml of methanol for 30 min, 0.51 g (yield: 84%) of the expected product is obtained after purification by chromatography on silica gel using a chloroform/methanol mixture (12/1 v/v) as the eluent, and lyophilization.
M.p.=102°-105° C.
$[\alpha]D^{21°\ C.} = -90°$ (c=0.44; CH$_3$OH)

PREPARATION IC

Preparation of 2-(6-cyanonaphthalenyl) 2,3,4-tri-O-acetyl-5-thio-β-D-xylopyranoside (Example 30a)

If the procedure described in Preparation LXXXIII is followed starting from 1.69 g (10.10$^{-3}$ mol) of 6-hydroxynaphthalene-2-carbonitrile, 1.75 g (10.10$^{-3}$ mol) of silver imidazolate, 3.87 g (11.1.10$^{-3}$ mol) of 2,3,4-tri-O-acetyl-5-thio-α-D-xylopyranosyl bromide and 2.7 g (19.7.10$^{-3}$ mol) of zinc chloride in 80 ml of methylene chloride, 0.72 g (yield: 16%) of the expected product is obtained after purification by chromatography on silica gel using a hexane/ethyl acetate mixture (3/1 v/v) as the eluent, and precipitation in ether.
M.p.=194° C.
$[\alpha]D^{21°\ C.} = -57.4°$ (c=0.5; CHCl$_3$)

PREPARATION C

Preparation of 2-(6-cyanonaphthalenyl) 5-thio-β-D-xylopyranoside (Example 30)

If the procedure described in Preparation LXXXIV is followed starting from 0.92 g (2.1.10$^{-3}$ mol) of 2-(6-cyanonaphthalenyl) 2,3,4-tri-O-acetyl-5-thio-β-D-xylopyranoside and 0.2 ml of a solution of sodium methylate in methanol (8% w/v of Na), reacted in 40 ml of methanol with the addition of tetrahydrofuran until solubilization is complete, 0.59 g (yield: 90%) of the expected product is obtained after precipitation in ether and crystallization from methanol.
M.p.=209°-214° C.
$[\alpha]D^{21°\ C.} = -83°$ (c=0.2; CH$_3$OH)

PREPARATION CI

Preparation of 2-(1-cyanonaphthalenyl) 2,3,4-tri-O-acetyl-5-thio-β-D-xylopyranoside (Example 31a)

If the procedure described in Preparation LXXXIII is followed starting from 5 g ($29.5.10^{-3}$ mol) of 2-hydroxynaphthalene-1-carbonitrile, 4.8 g ($32.7.10^{-3}$ mol) of silver imidazolate, 10.5 g ($29.5.10^{-3}$ mol) of 2,3,4-tri-O-acetyl-5-thio-α-D-xylopyranosyl bromide and 12 g ($88.10^{-3}$ mol) of zinc chloride in 200 ml of methylene chloride, 3.85 g (yield: 29.4%) of the expected product are obtained after purification by chromatography on a silica column using a hexane/ethyl acetate mixture (7/3 v/v) as the eluent, followed by washing with ether.

M.p. = 192° C. (decomposition)
$[\alpha]_D^{24°}$ C. = −141.6° (c=0.3; CHCl$_3$)

PREPARATION CII

Preparation of 2-(1-cyanonaphthalenyl) 5-thio-β-D-xylopyranoside (Example 31)

If the procedure described in Preparation LXXXIV is followed starting from 3 g ($6.76.10^{-3}$ mol) of 2-(1-cyanonaphthalenyl) 2,3,4-tri-O-acetyl-5-thio-β-D-xylopyranoside and 1.2 ml of a solution of sodium methylate in methanol (8% w/v of Na), reacted in 70 ml of methanol for 3.5 h, 1.30 g (yield: 59%) of the expected product are obtained after recrystallization from a methanol/water mixture (5/1 v/v).

M.p. = 163°–164° C.
$[\alpha]_D^{24°}$ C. = +13° (c=0.29; CH$_3$OH)

PREPARATION CIII

Preparation of 4-acetamidophenyl 2,3,4-tri-O-acetyl-5-thio-β-D-xylopyranoside (Example 32a)

30 mg of 10% palladium-on-charcoal are added to a solution of 150 mg ($0.36.10^{-3}$ mol) of 4-nitrophenyl 2,3,4-tri-O-acetyl-5-thio-β-D-xylopyranoside in acetic anhydride, under a nitrogen atmosphere, and the reaction mixture obtained is then kept under hydrogen pressure ($3.5.10^5$ Pa) at 50° C. for 15 hours. After filtration, the mixture is evaporated to dryness under reduced pressure and the residue obtained is purified by chromatography using a methylene chloride/methanol mixture (98/2 v/v) as the eluent to give 80 mg (yield: 51%) of the expected product.

M.p. = 166° C.
$[\alpha]_D^{25°}$ C. = −34° (c=0.25; CHCl$_3$)

PREPARATION CIV

Preparation of 4-acetamidophenyl 5-thio-β-D-xylopyranoside (Example 32)

If the procedure described in Preparation LXXXIV is followed starting from 1.2 g ($2.8.10^{-3}$ mol) of 4-acetamidophenyl 2,3,4-tri-O-acetyl-5-thio-β-D-xylopyranoside and 70 μl of a solution of sodium methylate in methanol (8% w/v of Na), reacted in 100 cm$^3$ of methanol, 0.7 g (yield: 83%) of the expected product is obtained after purification by flash chromatography using a methylene chloride/methanol mixture (93/7 v/v) as the eluent.

M.p. = 238° C.
$[\alpha]_D^{25°}$ C. = −48.3° (c=0.145; DMSO)

Without implying a limitation, the compounds according to the invention have been collated in Tables I and I bis given below, Table I relating to the compounds of formula I having a phenylthioxyloside structure and Table I bis relating to the compounds of formula I having a naphthalenylthioxyloside structure.

The antithrombotic activity of the products according to the invention was demonstrated by means of the following operating protocol for venous thrombosis:

A venous stasis under hypercoagulation is produced according to the technique described by WESSLER et al. (J. Applied Physiol. 1959, p. 943-946). As in the technique described by J. HAUPMAN et al. (Thrombosis and Haemostasis 43(2), 1980, p. 118), the hypercoagulant used is a solution of activated factor X (Xa) supplied by Flow Laboratories (71 Knat per 12.5 ml of physiological serum).

The study is performed on unfasted male Wistar rats weighing 250 to 280 g, divided into groups of 10 animals each. The products to be tested are administered orally as a suspension in PEG 400. A thrombosis is induced 4 hours after this treatment and the thrombus formed is removed and weighed.

The results obtained at doses of 3 mg/kg or 12.5 mg/kg, administered orally, have been collated in Table II. The results obtained with the known products of the above-mentioned prior art have also been collated in this Table.

The venous antithrombotic activity of the products according to the invention is distinctly superior to that of the known products of the prior art.

TABLE I (I)

[Structural formula with R$_1$, R$_2$, R$_3$ substituents on phenyl ring, X, S, OY groups on pyranose ring]

| Ex. | X | Y | R$_1$ | R$_2$ | R$_3$ |
|---|---|---|---|---|---|
| 1a | S | —COCH$_3$ | 4-CN | —H | —H |
| 1 | S | —H | 4-CN | —H | —H |
| 2a | S | —COCH$_3$ | 4-NO$_2$ | —H | —H |
| 2 | S | —H | 4-NO$_2$ | —H | —H |
| 4a | S | —COCH$_3$ | 4-CF$_3$ | —H | —H |
| 4 | S | —H | 4-CF$_3$ | —H | —H |
| 5a | S | —COCH$_3$ | 3-CN | —H | —H |
| 5 | S | —COCH$_3$ | 3-CN | —H | —H |
| 6a | S | —COCH$_3$ | 2-CN | —H | —H |
| 6 | S | —H | 2-CN | —H | —H |
| 7a | S | —COCH$_3$ | 2-NO$_2$ | —H | —H |
| 7 | S | —H | 2-NO$_2$ | —H | —H |
| 9a | S | —COCH$_3$ | —H | —H | —H |
| 9 | S | —H | —H | —H | —H |
| 10a | S | —COCH$_3$ | 3-OCH$_3$ | 4-OCH$_3$ | 5-OCH$_3$ |
| 10 | S | —H | 3-OCH$_3$ | 4-OCH$_3$ | 5-OCH$_3$ |
| 11a | S | —COCH$_3$ | 4-COCH$_3$ | —H | —H |
| 11 | S | —H | 4-COCH$_3$ | —H | —H |
| 12a | S | —COCH$_3$ | 3-NO$_2$ | —H | —H |
| 12 | S | —H | 3-NO$_2$ | —H | —H |
| 13a | S | —COCH$_3$ | 2-CF$_3$ | —H | —H |
| 13 | S | —H | 2-CF$_3$ | —H | —H |
| 14a | S | —COCH$_3$ | 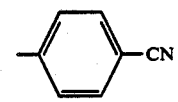 | —H | —H |

TABLE I-continued

| | | | | | |
|---|---|---|---|---|---|
| 14 | S | —H | 4-CN (phenyl) | —H | —H |
| 15a | S | —COCH₃ | 3-CF₃ | 5-CF₃ | —H |
| 15 | S | —H | 3-CF₃ | 5-CF₃ | —H |
| 16a | S | —COCH₃ | 2-CN | 4-CN | —H |
| 16 | S | —H | 2-CN | 4-CN | —H |
| 17a | S | —COCH₃ | 2-CN | 4-CN | 6-CN |
| 17 | S | —H | 2-CN | 4-CN | 6-CN |
| 18 | S | —H | 4-NH₂ | —H | —H |
| 19a | S | —COCH₃ | 4-NHCOCH₃ | —H | —H |
| 19 | S | —H | 4-NHCOCH₃ | —H | —H |
| 20a | S | —COCH₃ | 4-COCF₃ | —H | —H |
| 20 | S | —H | 4-COCF₃ | —H | —H |
| 21 | S | —H | 3-NH₂ | —H | —H |
| 22a | O | —COCH₃ | 4-CN | —H | —H |
| 22 | O | —H | 4-CN | —H | —H |
| 23a | O | —COCH₃ | 4-NO₂ | —H | —H |
| 23 | O | —H | 4-NO₂ | —H | —H |
| 24a | O | —COCH₃ | 4-COCH₃ | —H | —H |
| 24 | O | —H | 4-COCH₃ | —H | —H |
| 25a | O | —COCH₃ | 3-COCH₃ | —H | —H |
| 25 | O | —H | 3-COCH₃ | —H | —H |
| 26a | O | —COCH₃ | 2-CN | —H | —H |
| 26 | O | —H | 2-CN | —H | —H |
| 27a | O | —COCH₃ | 3-CN | —H | —H |
| 27 | O | —H | 3-CN | —H | —H |
| 28a | O | —COCH₃ | 2-NO₂ | —H | —H |
| 28 | O | —H | 2-NO₂ | —H | —H |
| 29a | O | —COCH₃ | 2-COCH₃ | —H | —H |
| 29 | O | —H | 2-COCH₃ | —H | —H |
| 32a | O | —COCH₃ | 4-NHCOCH₃ | —H | —H |
| 32 | O | —H | 4-NHCOCH₃ | —H | —H | bis

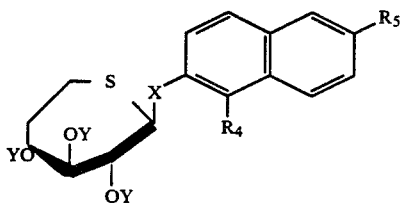

| Ex. | X | Y | R₄ | R₅ |
|---|---|---|---|---|
| 8 | S | —H | —H | —CN |
| 8a | S | —COCH₃ | —H | —CN |
| 30 | O | —H | —H | —CN |
| 30a | O | —COCH₃ | —H | —CN |
| 31 | O | —H | —CN | —H |
| 31a | O | —COCH₃ | —CN | —H |

TABLE II

| Example | % inhibition at 12.5 mg/kg | % inhibition at 3 mg/kg |
|---|---|---|
| 1a | 90 | 30 |
| 1 | 90 | 53 |
| 2 | 78 | 35 |
| 3 | 38 | — |
| 4 | 66 | — |
| 5 | 79.5 | 28 |
| 6 | 88.6 | 35 |
| 7 | 96.7 | 33 |
| 8 | 94.7 | 31 |
| 9 | 11 (1) | — |
| 10a | 62 | — |
| 10 | 36.5 | — |
| 11 | 98.3 | 47 |
| 12 | 69 | — |
| 13 | 23 | — |
| 14 | 86 | 27 |
| 16a | 72.8 | — |
| 16 | 99.5 | 42.5 |
| 17 | 40 | 8 |
| 18 | 93 | 30 |
| 19a | — | 66 |
| 19 | 93 | 61 |
| 20 | — | 49 |
| 21 | — | 31 |
| 22a | — | 66 |
| 22 | — | 57 |
| 23a | — | 44 |
| 23 | 94 | 37.5 |
| 24 | 100 | 55 |
| 25a | — | 52 |
| 25 | — | 44.5 |
| 26 | 96 | 63.5 |
| 27a | — | 57 |
| 27 | 98 | 66 |
| 28 | 94 | 51 |
| 29 | — | 26 |
| 30 | — | 51 |
| 31a | — | 44.5 |
| 31 | — | 28 |
| A | 14 (2) | |
| B | 5.5 | |

A: comparative product described in Example 1 of European patent document A-0133103
B: comparative product described in Example 97 of European patent document B-0051023
(1) 82 to 50 mg/kg administered orally
(1) 77 to 50 mg/kg administered orally

What is claimed is:

1. 4-Acetylphenyl 5-thio-β-D-xylopyranoside.
2. 3-Cyanophenyl 2,3,4-tri-O-acetyl-5-thio-β-D-xylopyranoside.
3. 3-Cyanophenyl 2,3,4-tri-O-acetyl-1,5-dithio-β-D-xylopyranoside.
4. 4-Acetamidophenyl 1,5-dithio-β-D-xylopyranoside.
5. An acylthioxylosyl trichloroacetimidate of the formula

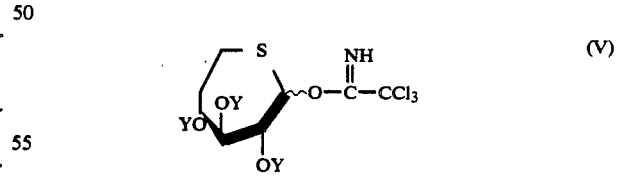

(V)

wherein Y is an acetyl group.

6. 4-acetylphenyl 2,3,4-tri-O-acetyl-5-thio-β-D-xylopyranoside.

UNITED STATES PATENT AND TRADEMARK OFFICE
CERTIFICATE OF CORRECTION

PATENT NO. : 5,101,048
DATED : March 31, 1992
INVENTOR(S) : Samreth et al It is certified that error appears in the above-identified patent and that said Letters Patent is hereby corrected as shown below:

See the attached sheets for replacement of the following formulas:

UNITED STATES PATENT AND TRADEMARK OFFICE
CERTIFICATE OF CORRECTION

PATENT NO. : 5,101,048

DATED : March 31, 1992

INVENTOR(S) : Samreth et al

It is certified that error appears in the above-identified patent and that said Letters Patent is hereby corrected as shown below:

Cover page, [57] Abstract, between lines 3 and 4, replace formula --(I)--

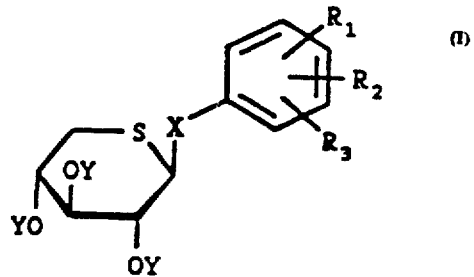

Column 1, between lines 35 -45, replace formula --(I)--

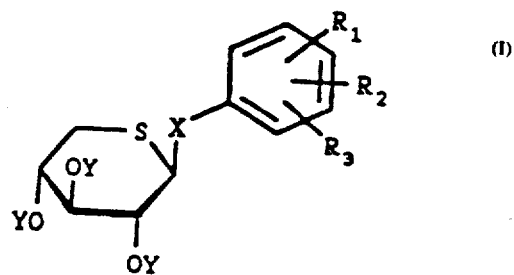

UNITED STATES PATENT AND TRADEMARK OFFICE
CERTIFICATE OF CORRECTION

PATENT NO. : 5,101,048

DATED : March 31, 1992

INVENTOR(S) : Samreth et al

It is certified that error appears in the above-identified patent and that said Letters Patent is hereby corrected as shown below:

Column 2, between lines 40 - 45, replace formula --(III)--

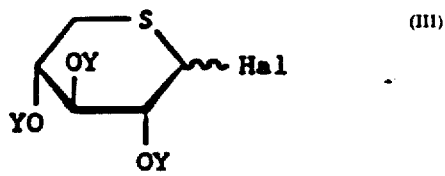

Column 2, between lines 50 - 55, replace formula --(IV)--

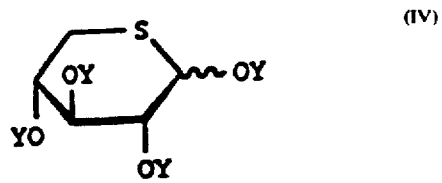

UNITED STATES PATENT AND TRADEMARK OFFICE
CERTIFICATE OF CORRECTION

PATENT NO.   : 5,101,048

DATED        : March 31, 1992

INVENTOR(S)  : Samreth et al

It is certified that error appears in the above-identified patent and that said Letters Patent is hereby corrected as shown below:

Column 2, between lines 60 - 65, replace formula --(V)--

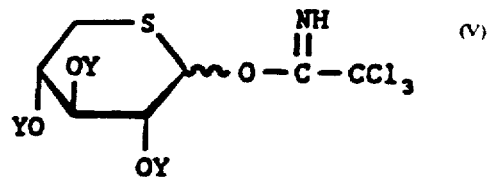

Column 30, between lines 33 - 42, replace formula --(I)--

TABLE I

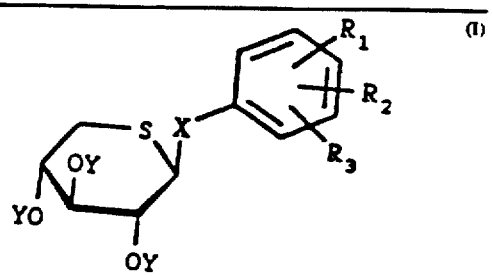

UNITED STATES PATENT AND TRADEMARK OFFICE
CERTIFICATE OF CORRECTION

PATENT NO. : 5,101,048

DATED : March 31, 1992

INVENTOR(S) : Samreth et al

It is certified that error appears in the above-identified patent and that said Letters Patent is hereby corrected as shown below:

Column 31, after "Table I-continued" replace formula.

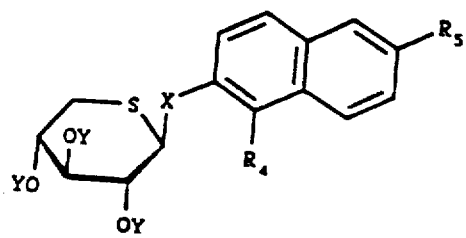

TABLE I bis

UNITED STATES PATENT AND TRADEMARK OFFICE
CERTIFICATE OF CORRECTION

PATENT NO. : 5,101,048

DATED : March 31, 1992

INVENTOR(S) : Samreth et al

It is certified that error appears in the above-identified patent and that said Letters Patent is hereby corrected as shown below:

Column 32, between lines 50 - 58, replace formula --(V)--

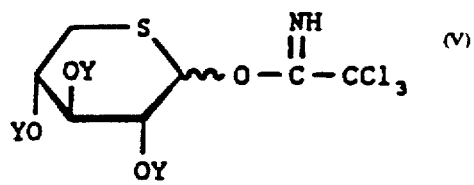

Signed and Sealed this

Fifth Day of January, 1993

*Attest:*

DOUGLAS B. COMER

*Attesting Officer*    Acting Commissioner of Patents and Trademarks